(12) United States Patent
Vriezen et al.

(10) Patent No.: US 12,054,726 B2
(45) Date of Patent: Aug. 6, 2024

(54) TOMATO PLANT PRODUCING FRUIT HAVING IMPROVED RIPENING CHARACTERISTICS

(71) Applicant: Nunhems B.V., Nunhem (NL)

(72) Inventors: Wim Vriezen, Nunhem (NL); Pieter Wesselink, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 17/618,058

(22) PCT Filed: Jun. 10, 2020

(86) PCT No.: PCT/EP2020/066040
§ 371 (c)(1),
(2) Date: Dec. 10, 2021

(87) PCT Pub. No.: WO2020/249593
PCT Pub. Date: Dec. 17, 2020

(65) Prior Publication Data
US 2022/0307045 A1    Sep. 29, 2022

(30) Foreign Application Priority Data
Jun. 13, 2019   (EP) .................................... 19180086

(51) Int. Cl.
*A01H 5/08*     (2018.01)
*A01H 1/00*     (2006.01)
*A01H 6/82*     (2018.01)
*C12N 15/82*    (2006.01)

(52) U.S. Cl.
CPC ........... *C12N 15/8249* (2013.01); *A01H 1/00* (2013.01); *A01H 5/08* (2013.01); *A01H 6/825* (2018.05)

(58) Field of Classification Search
None
See application file for complete search history.

(56) References Cited

U.S. PATENT DOCUMENTS

2016/0017350 A1 *   1/2016   Bao .................... C12N 15/8271
                                                          435/412

FOREIGN PATENT DOCUMENTS

| EP | 0534858 A1 | 3/1993 |
| WO | 91/01375 A1 | 2/1991 |
| WO | 2016/205711 A1 | 12/2016 |
| WO | 2018/220581 A1 | 12/2018 |

OTHER PUBLICATIONS

Akbudak, et al., "In vitro and in vivo behavior of gamma-irradiated tomato (*Lycopersicon esculentum*) pollen", New Zealand Journal of Crop and Horticultural Science, vol. 37, Issue 4, 2009, pp. 361-367.
Alexander, et al., "Ethylene biosynthesis and action in tomato: a model for climacteric fruit ripening", Journal of Experimental Botany, vol. 53, Issue 377, Oct. 1, 2002, pp. 2039-2055.
Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Dec. 2011, pp. 1086-1099.
Antonio Tiezzi, "The pollen tube cytoskeleton", Electron Microscopy Reviews, vol. 4, Issue 2, 1991, pp. 205-219.
Barry, et al., "Ethylene and Fruit Ripening", Journal of Plant Growth Regulation, vol. 26, Issue 2, Jun. 6, 2007, pp. 143-159.
Brooks, et al., "Efficient Gene Editing in Tomato in the First Generation Using the Clustered Regularly Interspaced Short Palindromic Repeats/CRISPR-Associated9 System", Plant Physiology, vol. 166, Issue 3, Sep. 15, 2014, pp. 1292-1297.
Bui, et al., "Postharvest Ripening Characterization of Greenhouse Tomatoes", International Journal of Food Properties, vol. 13, Issue 4, Mar. 30, 2010, pp. 830-846.
Comai, et al., "Efficient discovery of DNA polymorphisms in natural populations by Ecotilling", The Plant Journal, vol. 37, Issue 5, Feb. 10, 2004, pp. 778-786.
European Search Report for EP Patent Application No. 19180086.1, Issued on Nov. 4, 2019, 4 pages.
Fang, et al., "Getting Started in Gene Orthology and Functional Analysis", PLoS Computational Biology, vol. 6, Issue 3, Mar. 26, 2010, pp. 1-8.
Henikoff, et al., "Amino acid substitution matrices from protein blocks", Proceedings of the National Academy of Sciences of the United States of America, vol. 89, Issue 22, Nov. 15, 1992, pp. 10915-10919.

(Continued)

*Primary Examiner* — Phuong T Bui
(74) *Attorney, Agent, or Firm* — Arentfox Schiff LLP

(57) ABSTRACT

The present invention relates to a plant of the species *Solanum lycopersicum* comprising in its genome at least one copy of a mutant allele of the wild type ACO4 gene, wherein said mutant allele when present in homozygous form causes the fruits having an increased fruit firmness after the fruits entered the full red stage. The present invention further relates to a seed from which a plant according to present invention can be grown, a plant grown from the seed according to the present invention, a fruit produced by a plant according to the present invention and a part of a plant according to the present invention. The present invention further relates to a method for producing tomato fruit having an increased shelf life comprising growing a plant according to the present invention. The present invention further relates to a method of identifying and/or selecting a plant or plant part according to the present invention. The present invention further relates to a method of producing a plant of the species *Solanum lycopersicum* comprising in its genome at least one copy of a mutant allele of the ACO4 gene according to the present invention. The present invention further relates to the use of a plant of the species *Solanum lycopersicum* of the present invention for consumption or as a source of propagation material.

17 Claims, 3 Drawing Sheets
Specification includes a Sequence Listing.

(56) References Cited

OTHER PUBLICATIONS

Henikoff, et al., "Tilling. Traditional Mutagenesis Meets Functional Genomics", Plant Physiology, vol. 135, Issue 2, Jun. 18, 2004, pp. 630-636.
International Search Report for PCT Patent Application No. PCT/EP2020/066040, Issued on Jul. 31, 2020, 5 pages.
Jafari, et al., "Cloning, identification and expression analysis of ACC oxidase gene involved in ethylene production pathway", Molecular Biology Reports, vol. 40, Issue 2, Oct. 18, 2012, pp. 1341-1350.
Martínez-Madrid, et al., "Polyamine levels and ethylene production in tomato fruit development and ripening", I International Symposium on Solanacea for Fresh Market, ISHS Acta Horticulturae, vol. 412, 1995, pp. 463-469.
Morita, et al., "Molecular characterization of mutations induced by gamma irradiation in rice", Genes & Genetic Systems, vol. 84, Issue 5, 2009, pp. 361-370.
Mutschler, et al., "Tomato Fruit Quality and Shelf Life in Hybrids Heterozygous for the alc Ripening Mutant", HortScience, vol. 27, Issue 4, Apr. 1992, pp. 352-355.
Nakatsuka, et al., "Differential Expression and Internal Feedback Regulation of 1-Aminocyclopropane-1-Carboxylate Synthase, 1-Aminocyclopropane-1-Carboxylate Oxidase, and Ethylene Receptor Genes in Tomato Fruit during Development and Ripening", Plant Physiology, vol. 118, Issue 4, Dec. 1, 1998, pp. 1295-1305.
Ng, et al., "SIFT: predicting amino acid changes that affect protein function", Nucleic Acids Research, vol. 31, Issue 13, Jul. 1, 2003, pp. 3812-3814.
Stearns, et al., "Transgenic plants with altered ethylene biosynthesis or perception", Biotechnology Advances, vol. 21, Issue 3, May 2003, pp. 193-210.
Till, et al., "A protocol for Tilling and Ecotilling in plants and animals", Nature Protocols, vol. 1, Issue 5, Dec. 29, 2006, pp. 2465-2477.
Till, et al., "Chapter 11: High-Throughput Tilling for *Arabidopsis*", *Arabidopsis* Protocols, Methods in Molecular Biology, ed. Salinas, et al., 2nd edition, vol. 323, 2006, pp. 127-135.
Till, et al., "Discovery of chemically induced mutations in rice by Tilling", BMC Plant Biology, vol. 7, Issue 1, Article No. 19, Apr. 11, 2007, 12 pages.
Till, et al., "Discovery of induced point mutations in maize genes by Tilling", BMC Plant Biology, vol. 4, Issue 1, Article No. 12, Jul. 28, 2004, 8 pages.
Van De Poel, et al., "Targeted Systems Biology Profiling of Tomato Fruit Reveals Coordination of the Yang Cycle and a Distinct Regulation of Ethylene Biosynthesis during Postclimacteric Ripening", Plant Physiology, vol. 160, Issue 3, Sep. 13, 2012, pp. 1498-1514.
Xiong, et al., "Different effects on ACC oxidase gene silencing triggered by RNA interference in transgenic tomato", Plant Cell Reports, vol. 23, Issue 9, Oct. 19, 2004, pp. 639-646.

* cited by examiner

SEQUENCE LISTING

<160> NUMBER OF SEQ ID NOS: 4

<210> SEQ ID NO 1
<211> LENGTH: 316
<212> TYPE: PRT
<213> ORGANISM: Solanum lycopersicum

<400> SEQUENCE: 1

Met Glu Asn Phe Pro Ile Ile Asn Leu Glu Asn Leu Asn Gly Asp Glu
1               5                   10                  15

Arg Ala Lys Thr Met Glu Met Ile Lys Asp Ala Cys Glu Asn Trp Gly
            20                  25                  30

Phe Phe Glu Leu Val Asn His Gly Ile Pro His Glu Val Met Asp Thr
        35                  40                  45

Val Glu Lys Leu Thr Lys Gly His Tyr Lys Lys Cys Met Glu Gln Arg
    50                  55                  60

```
Phe Lys Glu Leu Val Ala Ser Lys Gly Leu Glu Ala Val Gln Ala Glu
 65                  70                  75                  80

Val Thr Asp Leu Asp Trp Glu Ser Thr Phe Phe Leu Arg His Leu Pro
                 85                  90                  95

Thr Ser Asn Ile Ser Gln Val Pro Asp Leu Asp Glu Glu Tyr Arg Glu
            100                 105                 110

Val Met Arg Asp Phe Ala Lys Arg Leu Glu Lys Leu Ala Glu Glu Leu
        115                 120                 125

Leu Asp Leu Leu Cys Glu Asn Leu Gly Leu Glu Lys Gly Tyr Leu Lys
    130                 135                 140

Asn Ala Phe Tyr Gly Ser Lys Gly Pro Asn Phe Gly Thr Lys Val Ser
145                 150                 155                 160

Asn Tyr Pro Pro Cys Pro Lys Pro Asp Leu Ile Lys Gly Leu Arg Ala
                165                 170                 175

His Thr Asp Ala Gly Gly Ile Ile Leu Leu Phe Gln Asp Asp Lys Val
            180                 185                 190

Ser Gly Leu Gln Leu Leu Lys Asp Glu Gln Trp Ile Asp Val Pro Pro
        195                 200                 205

Met Arg His Ser Ile Val Val Asn Leu Gly Asp Gln Leu Glu Val Ile
    210                 215                 220

Thr Asn Gly Lys Tyr Lys Ser Val Met His Arg Val Ile Ala Gln Thr
225                 230                 235                 240

Asp Gly Thr Arg Met Ser Leu Ala Ser Phe Tyr Asn Pro Gly Asn Asp
                245                 250                 255

Ala Val Ile Tyr Pro Ala Pro Ser Leu Ile Glu Glu Ser Lys Gln Val
            260                 265                 270

Tyr Pro Lys Phe Val Phe Asp Asp Tyr Met Lys Leu Tyr Ala Gly Leu
        275                 280                 285

Lys Phe Gln Pro Lys Glu Pro Arg Phe Glu Ala Met Lys Ala Met Glu
    290                 295                 300

Ala Asn Val Glu Leu Val Asp Gln Ile Ala Ser Ala
305                 310                 315

<210> SEQ ID NO 2
<211> LENGTH: 951
<212> TYPE: DNA
<213> ORGANISM: Solanum lycopersicum

<400> SEQUENCE: 2
atggagaact tcccaattat caacttggaa atcttaatg gagatgagag agccaaaacc      60
atggaaatga tcaaagatgc atgtgagaat tggggcttct ttgagttggt gaaccatggg     120
attccacatg aagtaatgga cactgtggag aaattgacaa agggacatta caagaagtgc     180
atggaacaga ggtttaagga attggtagca agtaagggac ttgaagctgt gcaagctgag     240
gttactgatt tagattggga agcacttttc ttcttgcgcc atcttcctac ttctaatatc     300
tctcaagtac ccgatcttga cgaagaatac agagaggtga tgagagattt tgctaaaaga     360
ttggagaagt tggctgagga gttacttgac ttactctgtg aaaatcttgg acttgaaaaa     420
ggttatttga aaaatgcctt ttatggatca aaaggtccca atttcggtac aaagttagc      480 aactatccac catgtcctaa gcccgatttg atcaagggac tccgcgctca tacagacgca     540
ggaggcatca tacttctgtt ccaagatgac aaagtgagtg gccttcaact cctcaaagac     600
gagcaatgga tcgatgttcc tcccatgcgc cactctattg tggttaacct tggtgaccag     660
cttgaggtga ttaccaacgg gaagtacaag agcgtgatgc acagagtgat tgcacaaaca     720
```

```
gatgggactc ggatgtcact agcatcattt tataatccag gaaatgacgc ggtgatctat     780
ccagcaccat ctctaattga ggaaagcaag caagtttatc cgaaattcgt gtttgatgat     840
tacatgaagt tatatgctgg actaaagttt cagccaaaag agccaagatt tgaagcaatg     900
aaggctatgg aagctaatgt ggaattagtt gatcaaattg caagtgctta a              951
```

```
<210> SEQ ID NO 3
<211> LENGTH: 202
<212> TYPE: PRT
<213> ORGANISM: Solanum lycopersicum

<400> SEQUENCE: 3
```

| | | | | | | | | | | | | | | |
|---|---|---|---|---|---|---|---|---|---|---|---|---|---|---|
| Met | Glu | Asn | Phe | Pro | Ile | Ile | Asn | Leu | Glu | Asn | Leu | Asn | Gly | Asp | Glu |
| 1 | | | | 5 | | | | | 10 | | | | | 15 | |

Arg Ala Lys Thr Met Glu Met Ile Lys Asp Ala Cys Glu Asn Trp Gly
         20                  25                  30

Phe Phe Glu Leu Val Asn His Gly Ile Pro His Glu Val Met Asp Thr
     35                  40                  45

Val Glu Lys Leu Thr Lys Gly His Tyr Lys Lys Cys Met Glu Gln Arg
 50                  55                  60

Phe Lys Glu Leu Val Ala Ser Lys Gly Leu Glu Ala Val Gln Ala Glu
65                  70                  75                  80

Val Thr Asp Leu Asp Trp Glu Ser Thr Phe Phe Leu Arg His Leu Pro
                 85                  90                  95

Thr Ser Asn Ile Ser Gln Val Pro Asp Leu Asp Glu Glu Tyr Arg Glu
            100                 105                 110

Val Met Arg Asp Phe Ala Lys Arg Leu Glu Lys Leu Ala Glu Glu Leu
        115                 120                 125

Leu Asp Leu Leu Cys Glu Asn Leu Gly Leu Glu Lys Gly Tyr Leu Lys
    130                 135                 140

Asn Ala Phe Tyr Gly Ser Lys Gly Pro Asn Phe Gly Thr Lys Val Ser
145                 150                 155                 160

Asn Tyr Pro Pro Cys Pro Lys Pro Asp Leu Ile Lys Gly Leu Arg Ala
                165                 170                 175

His Thr Asp Ala Gly Gly Ile Ile Leu Leu Phe Gln Asp Asp Lys Val
            180                 185                 190

Ser Gly Leu Gln Leu Leu Lys Asp Glu Gln
        195                 200

```
<210> SEQ ID NO 4
<211> LENGTH: 951
<212> TYPE: DNA
<213> ORGANISM: Solanum lycopersicum
<400> SEQUENCE: 4
atggagaact tcccaattat caacttggaa atcttaatg gagatgagag agccaaaacc       60
atggaaatga tcaaagatgc atgtgagaat tggggcttct tgagttggt gaaccatggg      120 attccacatg aagtaatgga cactgtggag aaattgacaa agggacatta caagaagtgc     180
atggaacaga ggtttaagga attggtagca agtaagggac ttgaagctgt gcaagctgag     240
gttactgatt tagattggga aagcactttc ttcttgcgcc atcttcctac ttctaatatc     300
tctcaagtac ccgatcttga cgaagaatac agagaggtga tgagagattt tgctaaaaga     360
ttggagaagt tggctgagga gttacttgac ttactctgtg aaaatcttgg acttgaaaaa     420
ggttatttga aaaatgcctt ttatggatca aaaggtccca atttcggtac taaagttagc     480
```

-continued

```
aactatccac catgtcctaa gcccgatttg atcaagggac tccgcgctca tacagacgca      540
ggaggcatca tacttctgtt ccaagatgac aaagtgagtg gccttcaact cctcaaagac      600
gagcaataga tcgatgttcc tcccatgcgc cactctattg tggttaacct tggtgaccag      660
cttgaggtga ttaccaacgg gaagtacaag agcgtgatgc acagagtgat tgcacaaaca      720
gatgggactc ggatgtcact agcatcattt tataatccag gaaatgacgc ggtgatctat      780
ccagcaccat ctctaattga ggaaagcaag caagtttatc cgaaattcgt gtttgatgat      840
tacatgaagt tatatgctgg actaaagttt cagccaaaag agccaagatt tgaagcaatg      900
aaggctatgg aagctaatgt ggaattagtt gatcaaattg caagtgctta a              951
```

TOMATO PLANT PRODUCING FRUIT HAVING IMPROVED RIPENING CHARACTERISTICS

CROSS-REFERENCE TO RELATED APPLICATIONS

This application is a National Stage Entry of PCT/EP2020/066040, filed Jun. 10, 2020, which claims priority to EP Application No. 19180086.1, filed Jun. 13, 2019, the disclosures of each of which are hereby incorporated by reference in their entirety.

FIELD OF THE INVENTION

This invention relates to the field of plant breeding. In particular to a plant of the species Solanum lycopersicum comprising in its genome at least one copy of a mutant allele of the wild type ACO4 gene, wherein said mutant allele when present in homozygous form causes the fruits having an increased fruit firmness after the fruits entered the full red stage. The present invention further relates to a seed from which a plant according to present invention can be grown, a plant grown from the seed according to the present invention, a fruit produced by a plant according to the present invention and a part of a plant according to the present invention. The present invention further relates to a method for producing tomato fruit having an increased shelf life comprising growing a plant according to the present invention. The present invention further relates to a method of identifying and/or selecting a plant or plant part according to the present invention. The present invention further relates to a method of producing a plant of the species Solanum lycopersicum comprising in its genome at least one copy of a mutant allele of the ACO4 gene according to the present invention. The present invention further relates to the use of a plant of the species Solanum lycopersicum of the present invention for consumption or as a source of propagation material.

BACKGROUND

Breeding of plants of the species Solanum lycopersicum aims at the production of commercial varieties optimally adapted to growing and storage conditions. A challenge that breeders are facing is finding an improved balance between fruit firmness post-harvest and consumer desires of taste, texture and colour. These consumer desires relate strongly to fruit ripening. Fruit ripening is a complex developmental process responsible for the transformation of the seed-containing organ into a tissue attractive to seed.

The changes associated with fruit ripening, in particular post-harvest softening, limit the shelf life of fresh tomatoes.

For tomato fruit growth and development, a number of consecutive phases can be discerned. After floral development (first phase) and pollination (second phase), early fruit development takes place (third phase), which is characterised by a high frequency of cell division after which the fruit rapidly increases in size, mainly due to cell expansion. At the end of the third phase the fruit reaches the mature green stage (fourth phase). During the fourth phase, fruit ripening takes place, which is characterised by a change in colour and flavour as well as fruit firmness and texture.

The build-up of the characteristic red colour of the tomato fruit is caused by the accumulation of lycopene and carotene. In general, different colouration phases are distinguished during tomato fruit development: mature green, breaker, orange and full red. At the breaker stage, the typical red pigmentation initiates. The full red stage is the stage where the fruit has reached its mature colour on the major part of the fruit.

In addition to the colour changes during fruit ripening, enzymatic activity leads to degradation of the middle lamellar region of the cell walls which leads to cell loosening which is manifested as softening and loss of texture of the fruit. Softening of the fruit is often measured as external resistance to compression, which can be quantified for example by a penetrometer.

Ripening and senescence in climacteric fruits such as tomatoes are promoted by ethylene. Two systems have been proposed to operate in climacteric plants regulating ethylene production. The first system is functional during normal vegetative growth. System 1 is auto inhibitory and responsible for production of basal ethylene levels that are detected in all tissues including those in non-climacteric plants. System 1 continues during fruit development until a competence to fruit ripening is attained. Then a transition period is reached that is characterized by an increase in the level of ethylene. This increased ethylene level induces system 2, which is active during the ripening of climacteric fruit. In system 2 ethylene production is autocatalytic.

Ethylene is autocatalytic for its own biosynthesis through increases in 1-aminocyclopropane-1-carboxylic acid (ACC) synthase (ACS) and ACC oxidase (ACO) activity. The biosynthesis of ethylene is for example described by Stearns and Glick (Biotechnology Advances 2003, vol 21 pp 193-210), which is incorporated herein by reference.

ACC synthase (ACS) is an enzyme that catalyses the synthesis of 1-aminocyclopropane-1-carboxylic acid (ACC) from S-Adenosyl methionine. ACS is also referred to as 1-aminocyclopropane-1-carboxylate synthase; Le-ACS; or S-adenosyl-L-methionine methylthioadenosine-lyase. At least eight ACS genes (LeACS1A, LeACS1B, and LeACS2-7) have been identified in tomato (Alexander et. al. (2002) Journal of Experimental Botany, Vol 53, No 377, pp 2039-2055) and each ACS gene has a different expression pattern.

ACC oxidase (ACO) is an enzyme that catalyses the conversion of ACC into ethylene. ACO is also referred to as 1-aminocyclopropane-1-carboxylate oxidase; Le-ACO or ethylene-forming enzyme. At least five ACO genes (LeACO1-5) have been identified in tomato, which are differentially expressed during fruit development and ripening (Van de Poel et al. (2013) Plant Physiology 160:1498-1514). During system 1, ACO1, ACO2 and ACO4 are expressed. During the transition period, ACO3 is transiently expressed. During system 2, particularly ACO1 and ACO5 expression is sharply increased, peaking at the orange stage. Only ACO1 continues to be expressed at elevated levels in the post-climacteric stage of fruit ripening; see e.g. FIG. 12 of Van de Poel et al. (Loc cit.). There is no clear consensus about the expression level of ACO4 during fruit ripening and fruit senescence in tomato. Van de Poel et al. (Loc cit.) report that ACO4 expression is very low during fruit ripening and post-harvest storage, while others have reported an increased expression or sustained expression of ACO4 during tomato fruit ripening (Jafari et al. (2013) Molecular Biology Reports 40:1341-1350; Nakatsuka et al. (1998) Plant Physiology 118:1295-1305). The exact role of each of the individual ACO isoforms and particularly of ACO4 in tomato fruit ripening and tomato fruit senescence thus is not known. In any case, multiple different ACO isoforms in tomato show a relatively high gene expression during fruit ripening in combination with a high redundancy between the different tomato ACO isoforms.

Modification of single genes known to be involved in ripening has not yet resulted in a tomato fruit with normal ripening and particularly normal fruit colour change, but minimal tissue softening during fruit ripening and fruit senescence. There is thus a need for cultivated tomato plants with a modified ethylene production having normal fruit development and fruit ripening, particularly normal colour development, in combination with an improved development of fruit firmness during fruit ripening and fruit senescence and/or a longer shelf-life of the tomato fruits when compared to fruits produced by wild type tomato plants.

SUMMARY OF INVENTION

The present invention relates to a plant of the species *Solanum lycopersicum* comprising in its genome at least one copy of a mutant allele of the wild type ACO4 gene, wherein said mutant allele results in a reduced expression or no expression of the wild type ACO4 gene and/or wherein the mutant allele encodes a protein having a decreased function or loss-of-function when compared to the wild type protein; and wherein the wild type ACO4 gene encodes a protein comprising at least 95% amino acid sequence identity to SEQ ID NO: 1.

The present invention further relates to a seed from which a plant according to present invention can be grown, a plant grown from said seed, a fruit produced by a plant of the present invention and a part of a plant according to the present invention, wherein said plant part preferably is a leaf, anther, pistil, stem, petiole, root, ovule, pollen, protoplast, tissue, seed, flower, cotyledon, hypocotyl, embryo or cell.

In addition, the present invention relates to a method producing tomato fruit having an increased shelf life, said method comprising growing a plant according to the present invention and harvesting the fruits produced by said plants. The present invention further relates to a method of identifying and/or selecting a plant or plant part of the species *Solanum lycopersicum* comprising a mutant allele of the wild type ACO4 gene comprising determining whether the plant or plant part comprises a mutant allele of the ACO4 gene, wherein said mutant allele results in a reduced expression or no expression of the wild type ACO4 gene or wherein the mutant allele encodes a protein having a decreased function or loss-of function when compared to the wild type protein and optionally selecting a plant or plant part comprising at least one copy of a mutant allele of the ACO4 gene wherein said mutant allele results in a reduced expression or no expression of the wild type ACO4 gene or wherein the mutant allele encodes a protein having a decreased function or loss-of function when compared to the wild type protein, wherein the wild type ACO4 gene encodes a protein comprising at least 95% amino acid sequence identity to SEQ ID NO:1. The present invention further relates to a method for producing a plant of the species *Solanum lycopersicum* comprising in its genome at least one copy of the mutant allele of the ACO4 gene as defined herein, wherein said mutant allele results in a reduced expression or no expression of the wild type ACO4 gene or wherein the mutant allele encodes a protein having a decreased function or loss-of function when compared to the wild type protein, said method comprising the step(s) of: (i) crossing a first *Solanum lycopersicum* plant and a second plant, wherein the first *Solanum lycopersicum* plant is the plant according to the present invention; (ii) optionally harvesting seed from the crossing of (i) and selecting seed comprising in its genome at least one copy of a mutant allele of the ACO4 gene as described herein.

In addition, the present invention relates to the use of a plant according to the present invention, preferably comprising a mutant aco4 allele in homozygous form, as a crop for producing fruits for consumption. The present invention further relates to the use of a plant according to the present invention as a source of propagation material.

BRIEF DESCRIPTION OF THE SEQUENCE LISTING

SEQ ID NO: 1 shows the amino acid sequence of a wild type *Solanum lycopersicum* ACO4 protein.
SEQ ID NO: 2 shows a nucleotide sequence (coding DNA or cDNA) encoding a wild type *Solanum lycopersicum* ACO4 protein.
SEQ ID NO: 3 shows the amino acid sequence of a mutant *Solanum lycopersicum* aco4 protein.
SEQ ID NO: 4 shows a nucleotide sequence (coding DNA or cDNA) encoding a mutant *Solanum lycopersicum* aco4 protein.

DETAILED DESCRIPTION OF THE INVENTION

General Definitions

Figure 1:
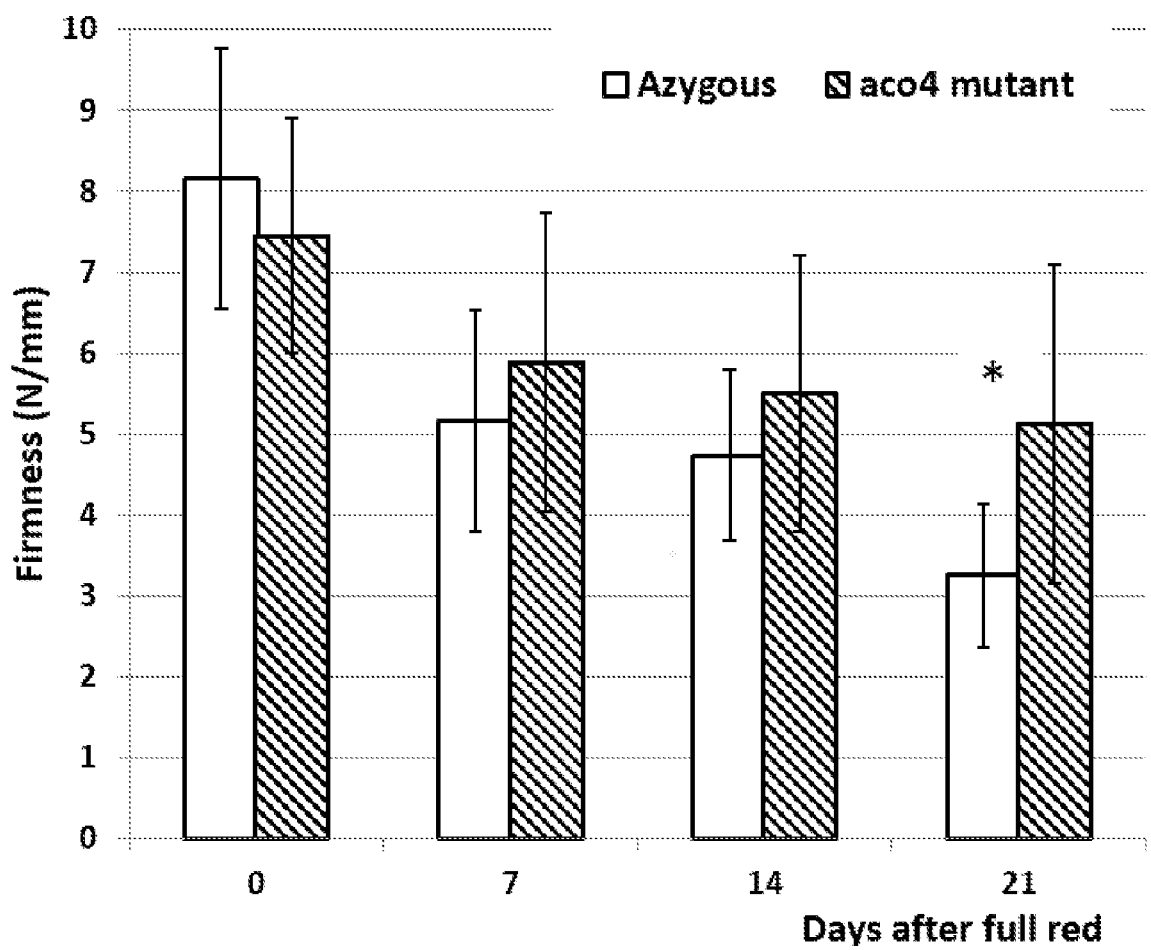
FIG. 1: Comparison of fruit firmness over time between aco4-mutant plants (aco4/aco4 plants) and azygous plants (ACO4/ACO4 plants). Fruits were measured at the day they became full red (0 days after full red) or 7, 14 or 21 days after becoming full red. White bars represents azygous fruit firmness (n=16), and hatched bars aco4-mutant fruit firmness (n=24) in Newton (N) per millimetre (mm). The error bars are SD. *P<0.05 Student's T-test.

The term "genome" relates to the genetic material of an organism. It consists of DNA. The genome includes both the genes and the non-coding sequences of the DNA.

The term "genetic determinant" relates to the genetic information in the genome of the plant that causes a particular trait of a plant. Accordingly, a genetic determinant comprises the genetic information (gene or locus or introgression) that confers a certain trait. In general, a genetic determinant may comprise a single gene (or one Quantitative Trait Locus (QTL)) or more than one gene. In the present invention, the genetic determinant comprises a single gene.

An allelism test is a test known in the art that can be used to identify whether two genes conferring the same trait are located at the same locus.

The word "trait" in the context of this application refers to the phenotype of the plant. When a plant shows the traits of the invention, its genome comprises the mutant allele causing the trait of the invention, particularly in the present invention when the mutant allele is in homozygous form. The plant, thus, has the genetic determinant of the invention. It is understood that when referring to a plant comprising the trait of the plant of the invention, reference is made to a *Solanum lycopersicum* plant comprising the trait of an increased fruit firmness as further described herein.

A genetic determinant can be inherited in a recessive manner, an intermediate manner, or in a dominant manner. Selection for the phenotypic trait is easier when intermediate or dominant inheritance is involved, as a larger part of the progeny of a cross reveals the trait. In general, a genetic determinant can also comprise a combination of recessive and/or intermediate and/or dominant genes or QTLs. In the present invention, the genetic determinant comprises a single recessive gene.

Selection for a genetic determinant (e.g. the mutant aco4 allele) can be done on phenotype (the trait that can be observed). Selection can also be done by using molecular genotyping methods, such as one or more molecular markers that are genetically linked to the mutant allele or preferably using the gene or allele sequence itself, e.g. by molecular methods which are able to distinguish between the presence of a mutant allele and wild type allele, or products thereof (such as mRNA or protein encoded by the allele). The use of molecular genotyping methods in breeding (such as "marker assisted selection" when genetically linked markers are used, or other genotyping methods, such as SNP genotyping) requires a smaller population for screening (when compared to phenotypical selection) and can be done in a very early stage. A further advantage of molecular genotyping methods is the possibility to easily distinguish between homozygous plants or seeds having no wild type copies of the ACO4 gene (homozygous for the mutant aco4 allele), heterozygous plants or seeds and homozygous plants or seeds having no copies of the mutant aco4 gene of the present invention, which can be done even before seeds germinate or in early plant development, e.g. before mature fruits have developed.

A "plant line" or "breeding line" refers to a plant and its progeny. As used herein, the term "inbred line" refers to a plant line which has been repeatedly selfed and is nearly homozygous for every characteristic. Thus, an "inbred line" or "parent line" refers to a plant which has undergone several generations (e.g. at least 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (plural loci) means a specific place or places or a site on a chromosome where for example a gene or genetic marker is found. The improved fruit firmness locus (or loci) of the present invention thus is the location(s) in the genome of a *Solanum lycopersicum* plant where the ACO4 gene is found.

The term "gene" means a (genomic) DNA sequence comprising a region (transcribed region), which is transcribed into a messenger RNA molecule (mRNA) in a cell, and an operably linked regulatory region (also described herein as regulatory sequence, e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein. A gene may be an endogenous gene (in the species of origin) or a chimeric gene (e.g. a transgene or cis-gene). The "promoter" of a gene sequence is defined as a region of DNA that initiates transcription of a particular gene. Promoters are located near the genes they transcribe, on the same strand and upstream on the DNA. Promoters can be about 100-1000 base pairs long. In one aspect the promoter is defined as the region of about 1000 base pairs or more e.g. about 1500 or 2000, upstream of the start codon (i.e. ATG) of the protein encoded by the gene.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

A "quantitative trait locus", or "QTL" is a chromosomal locus that encodes for one or more alleles that affect the expressivity of a continuously distributed (quantitative) phenotype.

"Physical distance" between loci (e.g. between molecular markers and/or between phenotypic markers) on the same chromosome is the actual physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Wild type allele" (WT) refers herein to a version of a gene encoding a fully functional protein (wild type protein). Accordingly, the term "wild type ACO4 allele" or "ACO4 allele" or "wild type allele of the ACO4 gene" refers to the fully functional allele of the ACO4 gene, which allows normal protein function (i.e. normal protein expression in combination with normal enzymatic activity of the expressed protein) when compared to a wild type ACO4 allele. The entire amino acid sequence of the wild type ACO4 protein is conserved as a dioxygenase. One domain of the wild type ACO4 protein is specific for the 2-oxoglutarate and a further protein domain is specific for the Fe(II)-dependent oxygenase superfamily. These domains are believed to be important for the in vivo activity of the protein. One example of a wild type ACO4 allele in the species *Solanum lycopersicum* for instance is the wild type genomic DNA which encodes the wild type ACO4 cDNA (mRNA) sequence depicted in SEQ ID NO:2. The protein sequence encoded by this wild type ACO4 cDNA has 316 amino acid residues and is depicted in SEQ ID NO:1, which corresponds to NCBI reference sequence NP_001233928.1. The wild type *Solanum lycopersicum* ACO4 allele further comprises functional variants of the wild type genomic DNA which encodes the wild type ACO4 cDNA and amino acid sequences as described herein. Whether a certain variant of the herein specifically described wild type ACO4 allele represents a "functional variant" can be determined by using routine methods, including, but not limited to, testing of enzymatic activity of the protein, phenotypic testing for normal fruit ripening and in silico prediction of amino acid changes that affect protein function. For instance, a web-based computer program SIFT (Sorting Intolerant From Tolerant) is a program that predicts whether an amino acid substitution affects protein function; see world wide web at sift.bii.a-star.edu.sg/. Functionally important amino acids will be conserved in the protein family, and so changes at well-conserved positions tend to be predicted as not tolerated or deleterious; see also Ng and Henikoff (2003) Nucleic Acids Res 31(13): 3812-3814. For example, if a position in an alignment of a protein family only contains the amino acid isoleucine, it is presumed that substitution to any other amino acid is selected against and that isoleucine is necessary for protein function. Therefore, a change to any other amino acid will be predicted to be deleterious to protein function. If a position in an alignment contains the hydrophobic amino acids isoleucine, valine and leucine, then SIFT assumes, in effect, that this position can only contain amino acids with hydrophobic character. At this position, changes to other hydrophobic amino acids are usually predicted to be tolerated but changes to other residues (such as charged or polar) will be predicted to affect protein function. An alternative tool useful for the prediction of protein function is Provean; see world wide web at provean.jcvi.org/index.php. Also an ortholog of the *Solanum lycopersicum* ACO4 gene, particularly in a wild relative of the species *Solanum lycopersicum*, may be a functional variant of the wild type ACO4 allele provided that said variant allows normal protein function.

"Mutant allele" refers herein to an allele comprising one or more mutations when compared to the wild type allele, resulting in the trait of the present invention. The one or more mutations may be in the coding sequence (mRNA, cDNA or genomic sequence) or in the associated non-coding sequence and/or regulatory sequence regulating the level of expression of the coding sequence. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein being truncated or having an amino acid sequence wherein one or more amino acids are deleted, inserted or replaced. Such changes may lead to the protein having a different 3D conformation, being targeted to a different sub-cellular compartment, having one or more modified catalytic domains, having a modified binding activity to nucleic acids or proteins, etc. Preferably, the mutant allele of the present invention encodes a protein having a mutation in the Fe(II)-dependent oxygenase domain resulting in a mutant protein having a decreased function or loss-of-function when compared to the wild type protein. More preferably, the mutant allele of the present invention encodes a protein having a stop mutation in the Fe(II)-dependent oxygenase domain resulting in a truncated protein having decreased function or loss-of-function when compared to the wild type protein. Furthermore, the mutation(s) (e.g. insertion, inversion, deletion and/or replacement of one or more nucleotide(s)) may lead to the encoded protein having reduced expression or no protein expression. Accordingly, the term "mutant aco4 allele" or "aco4 allele" or "mutant allele of the ACO4 gene" or "mutant allele of the wild type ACO4 gene" inter alia refers to an allele of the ACO4 gene comprising one or more mutations in the coding sequence, which one or more mutations leads to a reduced function or loss-of-function of encoded gene product and which causes the fruits having an increased fruit firmness after the fruits entered the full red stage when the mutant allele is in homozygous form. Such a mutant type aco4 allele in the species *Solanum lycopersicum* for instance is the mutant aco4 cDNA (mRNA) sequence depicted in SEQ ID NO:4. The protein sequence encoded by this mutant *Solanum lycopersicum* aco4 cDNA has 202 amino acids and is depicted in SEQ ID NO:3. The term mutant aco4 allele also comprises knock-out aco4 alleles and knock-down aco4 alleles, as well as aco4 alleles encoding a mutant aco4 protein having reduced function or no function. As used herein, the term "knock-out allele" refers to an allele wherein the expression of the respective (wild type) gene is not detectable anymore. A "knock-down" aco4 allele has reduced expression of the respective (wild type) gene compared to the wild type allele.

The term "induced mutant allele" as used herein refers to any allele of the wild type gene resulting in the trait of the present invention which is produced by human intervention, such as mutagenesis. Preferably, the induced mutant allele cannot be found in plants in the natural population or breeding population.

The term "natural mutant allele" as used herein refers to any allele of the wild type gene resulting in the trait of the present invention wherein the mutant allele evolved without human intervention. Preferably, the natural mutant allele can be found in plants in the natural population or breeding population.

"Wild type plant" refers herein to a plant of the family Solanaceae, preferably a plant of the species *Solanum lycopersicum*, comprising two copies of the wild type ACO4 allele and thus is considered to show normal fruit ripening. Such plants are for example suitable controls in phenotypic essays, particularly if said control plants have the same genetic background as the plants (e.g. mutant plants) that are subjected to phenotypic testing.

In a plant of the species *Solanum lycopersicum* the wild type ACO4 gene encodes a protein comprising at least 95% (96%, 97%, 98%, 98.3%, 98.7%, 99.0%, or 99.3% or more preferably 99.7%) amino acid sequence identity to SEQ ID NO:1. The protein described by the amino acid sequence SEQ ID NO:1 represents the wild type ACO4 protein *Solanum lycopersicum* and corresponds to NCBI reference sequence NP_001233928.1. In wild relatives *Solanum lycopersicum* the wild type ACO4 protein accordingly is encoded by an ortholog of the wild type ACO4 gene in *Solanum lycopersicum*. Preferably, the ortholog of the *Solanum lycopersicum* ACO4 gene in wild relatives of *Solanum lycopersicum* encodes a protein having at least 95% (e.g. at least 96%, 97%, 98%, 98.3%, 98.7%, 99.0%, or 99.3% or more preferably 99.7%) amino acid sequence identity to SEQ ID NO:1.

The term "orthologous gene" or "ortholog" is defined as genes in different species that have evolved through speciation events. It is generally assumed that orthologs have the same biological functions in different species. Accordingly, it is particularly preferred that the protein encoded by the ortholog of the wild type *Solanum lycopersicum* ACO4 gene in wild relatives of the species *Solanum lycopersicum* has the same biological function as the wild type *Solanum lycopersicum* ACO4 protein. Methods for the identification of orthologs is very well known in the art as it accomplishes two goals: delineating the genealogy of genes to investigate the forces and mechanisms of evolutionary process and creating groups of genes with the same biological functions (Fang G, et al (2010) Getting Started in Gene Orthology and Functional Analysis. PLoS Comput Biol 6(3): e1000703. doi:10.1371/journal.pcbi.1000703). For instance, orthologs of a specific gene or protein can be identified using sequence alignment or sequence identity of the gene sequence of the protein of interest with gene sequences of other species. Gene alignments or gene sequence identity determinations can be done according to methods known in the art, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.). In one aspect of the invention an ortholog of the *Solanum lycopersicum* ACO4 protein in wild relatives of *Solanum lycopersicum* has at least 95% (e.g. at least 96%, 97%, 98%, 98.3%, 98.7%, 99.0%, or 99.3% or more preferably 99.7%) amino acid sequence identity with SEQ ID NO: 1.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). It is understood that the term "introgression fragment" never includes a whole chromosome, but only a part of a chromosome. The introgression fragment can be large, e.g. even three-quarters or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

The term "isogenic plant" refers to two plants which are genetically identical except for the mutant allele of the present invention. In order to investigate the impact of an increased fruit firmness trait, one can cross a plant line (or variety) of interest with a plant comprising the mutant allele causing the increased fruit firmness trait and select for progeny expressing the desired trait. Optionally one may have to self the progeny one or more times to be able to determine the genetic determinants for the increased fruit firmness trait in the plant phenotype. Said progeny can then be backcrossed (at least 2 times, e.g. 3, 4, or preferably 5 or 6 times) with the plant line (or variety) of interest while selecting for progeny having the same phenotype as the plant line (or variety) of interest and expressing the genetic determinants for the increased fruit firmness trait. The impact of the mutant allele causing the increased fruit firmness trait can then be compared between the plant line (variety) of interest and its isogenic line not comprising the genetic determinants for the increased fruit firmness trait.

The term "nucleic acid sequence" or "nucleic acid molecule" or polynucleotide are used interchangeably and refer to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein", "peptide sequence", "amino acid sequence" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation results in (the mutant nucleic acid molecule encoding) a protein having altered activity, preferably a protein having reduced activity, most preferably a protein having no activity.

"Functional derivatives" of a protein as described herein are fragments, variants, analogues, or chemical derivatives of the protein which retain at least a portion of the activity or immunological cross reactivity with an antibody specific for the mutant protein.

A fragment of a mutant protein refers to any subset of the molecule.

Variant peptides may be made by direct chemical synthesis, for example, using methods well known in the art.

An analogue of a mutant protein refers to a non-natural protein substantially similar to either the entire protein or a fragment thereof.

A "mutation" in a nucleic acid molecule is a change of one or more nucleotides compared to the wild type sequence, e.g. by replacement, deletion or insertion of one or more nucleotides.

A "mutation" in an amino acid molecule making up a protein is a change of one or more amino acids compared to the wild type sequence, e.g. by replacement, deletion or insertion of one or more amino acids. Such a protein is then also referred to as a "mutant protein".

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a premature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made. The "promoter of a gene sequence", accordingly is defined as a region of DNA that initiates transcription of a particular gene. Promoters are located near the genes they transcribe, on the same strand and upstream on the DNA. Promoters can be about 100-1000 base pairs long. In one aspect, the promoter is defined as the region of about 2000 base pairs or more upstream of the start codon (i.e. ATG) of the protein encoded by the gene, preferably, the promoter is the region of about 1500 base pairs upstream of the start codon, more preferably the promoter is the region of about 1000 base pairs upstream of the start codon.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the nucleic acid sequences being linked are typically contiguous.

"Sequence identity" and "sequence similarity" can be determined by alignment of two peptide or two nucleotide sequences using global or local alignment algorithms. Sequences may then be referred to as "substantially identical" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, (as available on the Internet by ebi.ac.uk at world wide web at ebi.ac.uk under /Tools/psa/emboss_needle/). Alternatively, sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 95%, 96%, 97%, 98%, 98.3%, 98.7%, 99.0%, or 99.3% or more preferably 99.7% (as determined by Emboss "needle" using default parameters, i.e. gap creation penalty=10, gap extension penalty=0.5, using scoring matrix DNAFULL for nucleic acids and Blosum62 for proteins). Such sequences are also referred to as 'variants' herein, e.g. other variants of alleles causing the increased fruit firmness trait of the present invention and proteins than the specific nucleic acid and amino acid sequences disclosed herein can be identified, which have the same effect on an increased fruit firmness as the plants of the present invention The term "hybridisation" as used herein is generally used to mean hybridisation of nucleic acids at appropriate conditions of stringency (stringent hybridisation conditions) as would be readily evident to those skilled in the art depending upon the nature of the probe sequence and target sequences. Conditions of hybridisation and washing are well-known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, New York, 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1× Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature ($T_M$) of the duplex. The $T_M$ is known to be a function of the G-C content and duplex length as well as the ionic strength of the solution.

As used herein, the phrase "hybridizes" to a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridisation under appropriate conditions. For example, a 100 nucleotide long molecule from the 3' coding or non-coding region of a gene will recognize and hybridize to an approximately 100 nucleotide portion of a nucleotide sequence within the 3' coding or non-coding region of that gene or any other plant gene so long as there is about 70% or more sequence similarity between the two sequences. It is to be understood that the size of the corresponding portion will allow for some mismatches in hybridisation such that the corresponding portion may be smaller or larger than the molecule which hybridizes to it, for example 20-30% larger or smaller, preferably no more than about 12-15% larger or smaller.

As used herein, the phrase "a sequence comprising at least 95% sequence identity" or "a sequence comprising at least 95% amino acid sequence identity" or "a sequence comprising at least 95% nucleotide sequence identity" means a sequence having at least 95% e.g. at least 96%, 97%, 98%, 98.3%, 98.7%, 99.0%, or 99.3% or more preferably 99.7% sequence identity when compared with the reference sequence that is indicated. Sequence identity can be determined according the methods described herein.

A "fragment" of the gene or DNA sequence refers to any subset of the molecule, e.g., a shorter polynucleotide or oligonucleotide. In one aspect the fragment comprises the mutation as defined by the invention.

A "variant" of the gene or DNA refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. Preferably the variant comprises the mutant allele as defined by the invention.

As used herein, the term "plant" includes the whole plant or any parts or derivatives thereof, such as plant organs (e.g., harvested or non-harvested flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries (e.g., harvested tissues or organs), flowers, leaves, seeds, tubers, clonally propagated plants, roots, stems, cotyledons, hypocotyls, root tips and the like. Also any developmental stage is included, such as seedlings, immature and mature, etc. Preferably, the plant part or derivative comprises the gene or locus as defined by the current invention.

A "plant line" or "breeding line" refers to a plant and its progeny.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed, or hybrid) is the generation obtained from crossing two inbred parent lines. "Selfing", accordingly, refers to the self-pollination of a plant, i.e. to the union of gametes from the same plant.

"Backcrossing" refers to a breeding method by which a (single) trait, such as the capability for an increased fruit firmness, can be transferred from one genetic background (also referred to as "donor" generally, but not necessarily, this is an inferior genetic background) into another genetic background (also referred to as "recurrent parent"; generally, but not necessarily, this is a superior genetic background). An offspring of a cross (e.g. an F1 plant obtained by crossing a first plant of a certain plant species comprising the mutant allele of the present invention with a second plant of the same plant species or of a different plant species that can be crossed with said first plant species wherein said second plant species does not comprise the mutant allele of the present invention; or an F2 plant or F3 plant, etc., obtained by selfing the F1) is "backcrossed" to a parent plant of said second plant species. After repeated backcrossing, the trait of the donor genetic background, e.g. the mutant allele conferring the increased fruit firmness trait of the present invention, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes transferred from the donor parent. The plants grown from the seeds produced by backcrossing of the F1 plants with the second parent plant line is referred to as the "BC1 generation". Plants from the BC1 population may be selfed resulting in the BC1F2 generation or backcrossed again with the cultivated parent plant line to provide the BC2 generation. An "M1 population" is a plurality of mutagenized seeds/plants of a certain plant line. "M2, M3, M4, etc." refers to the consecutive generations obtained following selfing of a first mutagenized seed/plant (M1).

"Solanaceous plants" or "plants of the family Solanaceae" are plants of the botanical family Solanaceae, i.e. any plant of the family Solanaceae, including wild solanaceous plants and cultivated solanaceous plants. The botanical family Solanaceae consists about 98 genera of which the genera *Solanum* and *Capsicum* are the commercially most relevant as they comprise many domesticated species that are widely cultivated and used as food crops with high economic importance.

The genus *Solanum* consists of about 1330 species, including the highly important food crops *S. lycopersicum* (tomato), *S. melongena* (eggplant) and *S. tuberosum* (potato).

*Solanum lycopersicum* plants or "tomato plants" are further herbaceous plants of the family Solanaceae that are of particular relevance in the context of the present invention. Tomato plants are perennial in their native habitat but cultivated as an annual. Cultivated tomato plants typically grow to 1-3 meters (3-10 ft) in height. Tomato fruits are botanically berry-type fruits, they are considered culinary vegetables. Fruit size varies according to cultivar, with a width range of about 1-10 cm (about 0.5-4 inches). *Solanum lycopersicum* is also known as *Lycopersicon lycopersicum* (L.) H. Karst. or *Lycopersicon esculentum* Mill. The term "cultivated tomato plant" or "cultivated tomato" refers to plants of *Solanum lycopersicum*, e.g. varieties, breeding lines or cultivars of the species *S. lycopersicum*, cultivated by humans and having good agronomic characteristics. The term "wild relatives of *Solanum lycopersicum*" or "wild relatives of tomato" include *S. arcanum, S. chmielewskii, S. neorickii* (=*L. parviflorum*), *S. cheesmaniae, S. galapagense, S. pimpinellifolium, S. chilense, S. corneliomulleri, S. habrochaites* (=*L. hirsutum*), *S. huaylasense, S. sisymbnifolium, S. peruvianum, S. hirsutum* or *S. pennelli*. Tomato and the wild relatives of tomato is/are diploid and has/have 12 pairs of homologous chromosomes, numbered 1 to 12.

The term "cultivated plant" or "cultivar" refers to plants of a given species, e.g. varieties, breeding lines or cultivars of the said species, cultivated by humans and having good agronomic characteristics. The so-called heirloom varieties or cultivars, i.e. open pollinated varieties or cultivars commonly grown during earlier periods in human history and often adapted to specific geographic regions, are in one aspect of the invention encompassed herein as cultivated plants. The term "cultivated plant" does not encompass wild plants. "Wild plants" include for example wild accesions.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes substance consumed to provide nutritional support for both the human and animal body.

"Vegetative propagation" or "clonal propagation" refers to propagation of plants from vegetative tissue, e.g. by propagating plants from cuttings or by in vitro propagation. In vitro propagation involves in vitro cell or tissue culture and regeneration of a whole plant from the in vitro culture. Clones (i.e. genetically identical vegetative propagations) of the original plant can thus be generated by in vitro culture. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Average" refers herein to the arithmetic mean.

It is understood that comparisons between different plant lines involves growing a number of plants of a line (or variety) (e.g. at least 5 plants, preferably at least 10 plants per line) under the same conditions as the plants of one or more control plant lines (preferably wild type plants) and the determination of differences, preferably statistically significant differences, between the plant lines when grown under the same environmental conditions. Preferably the plants are of the same line or variety.

The "ripening stage" of a tomato fruit can be divided as follows: Mature green stage: surface is completely green; the shade of green may vary from light to dark, wherein the green colour may be further characterized as "144B" of the RHS Colour chart (Royal Horti-cultural Society, 2007). Breaker stage: there is a definite break in colour from green to tannish-yellow, pink or red on not more than 10% of the surface, wherein the colour at breaker stage may be further characterized as "N144D" of the RHS Colour chart (Royal Horticultural Society, 2007). Orange stage: 30% to 60% of the surface is not green; in the aggregate shows orange colour, wherein said orange colour may be further characterized as "N163C/D" of the RHS Colour chart (Royal Horticultural Society, 2007). Full Red stage: More than 90% of the surface is not green; in the aggregate, shows red colour, wherein said red colour may be further characterized as "44A/B" of the RHS Colour chart (Royal Horticultural Society, 2007). Fruit colour accordingly can be classified by comparing the colour of a given fruit to a colour chart like the Royal Horticultural Society (RHS) Colour Chart (world wide web at rhs.org.uk). Alternative methods for the classification of tomato fruit colour includes the application the U.S. standards for grades of fresh tomato (U.S. Dept of Agriculture, 1973, US standards for grades of fresh tomatoes, U.S. Dept Agr. Agr. Mktg. Serv., Washington D.C.), e.g. by measuring the colour with a chromometer (Mutschler et al, 1992, Horscience 27 pp 352-355).

The term "fruit firmness" refers to the capacity of a fruit to resist deformation resulting from the application of a defined mechanical force. Fruit firmness can for example be measured using the methods as described herein below in the examples. For instance, fruit firmness may be measured using a Single Column Tabletop Testing Systems (Instron, System ID: 3342L2018; Force Transducer model 2519-104) and Bluehill Software (Instron, 825 University Ave, Norwood, MA 02062-2643, USA). A tomato fruit is compressed between two flat steel plates with an incremental force from 0.1 Newton (N) to 4 N. Firmness measured as the force (N) necessary to compress fruits per millimetre by the Instron Force Transducer. Alternatively, fruit firmness can be measured by evaluating resistance to deformation in units of for example 0.1 mm as measured with a penetrometer fitted with a suitable probe (e.g. a probe of 3 mm) (Mutschler et al, 1992, Horscience 27 pp 352-355) (Marinez et al 1995 Acta Horticulturae 412 pp 463-469). Further alternative methods exist in the art, such as use of a texturometer (Bui et al. 2010; International Journal of Food Properties, Volume 13, Issue 4). As used herein, "increased fruit firmness" refers to (statistically significant) increased fruit firmness of certain tomato fruits, e.g. tomato fruits according to the invention, when compared to the tomato fruits of an appropriate control, e.g. wild type ACO4/ACO4 fruits, during a specific stage of fruit ripening, e.g. at the orange stage, at the full red stage and/or at a specific time point after the fruits entered the full red stage. A mutant plant (e.g. a plant homozygous for the mutant aco4 allele (aco4/aco4)) that produces fruits having an increased fruit firmness after the fruits entered the full red stage accordingly produces fruits wherein the average fruit firmness at a certain point of time after the fruits entered the full red stage is increased, preferably statistically significant increased, when compared to the average fruit firmness of the appropriate control fruits at the same point of time (e.g. 21 days) after the fruits entered the full red stage (e.g. fruits of plants homozygous for the wild type ACO4 allele (ACO4/ACO4)). A mutant plant (e.g. a plant homozygous for the mutant aco4 allele (aco4/aco4)) that produces fruits having an increased fruit firmness at 21 days after the fruits entered the full red stage accordingly produces fruits wherein the average fruit firmness at 21 days after the fruits entered the full red stage is increased, preferably statistically significant increased, when compared to the average fruit firmness of the appropriate control fruits at 21 days after the control fruits entered the full red stage (e.g. fruits of plants homozygous for the wild type ACO4 allele (ACO4/ACO4)).

The term "shelf life" or "post-harvest shelf life" designates the (average) length of time that a fruit is given before it is considered unsuitable for sale or consumption ('bad'). Shelf life is the period of time that products can be stored, during which the defined quality of a specified proportion of the goods remains acceptable under expected conditions of distribution, storage and display. Shelf life is influenced by several factors: exposure to light and heat, transmission of gases (including humidity), mechanical stresses, and contamination e.g. by micro-organisms. Product quality is often mathematically modelled around the fruit firmness/softness parameter. Shelf life can be defined as the (average) time it takes for fruits of a plant line to start to become bad and unsuitable for sale or consumption, starting for example from the first fruit of a plant entering breaker stage or from the first fruit entering the full red stage or from harvest. In one aspect the mutants according to the invention have a shelf life that is significantly longer than the shelf life of wild type plants, for example the number of days from the first fruit being in breaker stage (or the first fruit being in orange stage or the first fruit being in full red stage or from harvest) up to the first fruit starting to become 'bad' and unsuitable for sale or consumption is significantly longer, e.g. at least 1, 2, 3, 4, 5, 6, 7, 8, 9, 10, or more, days longer than fruits of control plants (such as wild type ACO4/ACO4 plants), when plants are grown under the same conditions and fruits are treated the same way and kept under the same conditions. Thus, to determine the number of days required from a certain stage (e.g. from breaker stage or orange stage or full red stage) to 'bad' stage, the day when the first fruit of the wild type control plant (grown under the same conditions as the mutant plants and being at the same developmental stage) enters a certain stage (e.g. breaker stage or a later stage or orange stage or full red stage) can, for example, be taken as the starting point (day 1) from when on periodically (at certain time intervals, e.g. after 1, 2, 3, 4, 5 or 6 days) the fruits are observed until the day that the first fruit has passed the full red stage and becomes 'bad' (as determinable visually and/or through assessing fruit firmness, e.g. as described herein). In this application the words "improved", "increased", "longer" and "extended" as used in conjunction with the word "shelf life" are interchangeable and all mean that the fruits of a tomato plant according to the invention have on average, a longer shelf-life than the control fruits (ACO4/ACO4 fruits).

"Delayed ripening" means that the fruits of a tomato plant or plant line (e.g. a mutant) require on average significantly more days to reach the full red stage from the mature green, breaker, and/or orange stages of tomato fruit ripening compared to wild type control fruits (e.g. fruits of plants homozygous for the wild type ACO4 allele (ACO4/ACO4). Delayed ripening can be measured on the plant and/or after harvest as days required for a certain percentage of fruits (e.g. 10%, 20%, 30%, 40%, 50%, 60%, 70%, 80%, 90% and/or 100% of fruits) to reach the full red stage. A plant is said to have a delayed ripening phenotype if it takes at least 2, 3, 4, 5, 6, 7, 8, 9, 10, 11, 12, 13, 14 or 15 days longer for 10%, 20%, 30% 40%, 50%, 60%, 70%, 80%, 90% and/or 100% of fruits to reach the full red stage than it takes for the wild type control fruits to develop the same percentage of red fruits. It is understood that each combination of above-cited number of days (i.e. 2, 3, 4, 5, 6, 7, 8, 9, 10, 11, 12, 13, 14 or 15) with each % of fruits to reach the red stage (i.e. 10%, 20%, 30% 40%, 50%, 60%, 70%, 80%, 90% and/or 100%) is enclosed herein, both for the delayed ripening to be measured on the plant and after harvest. For example if it takes at least 2 days longer for 10%, 20%, 30% 40%, 50%, 60%, 70%, 80%, 90% and/or 100% of fruits to reach the red stage than it takes for the wild type control fruits to develop the same percentage of red fruits. Another example of how delayed ripening can be measured on the plant and/or after harvest is it takes at least 2, 3, 4, 5, 6, 7, 8, 9, 10, 11, 12, 13, 14 or 15 days longer for 100% of fruits to reach the red stage than it takes for the wild type control fruits to develop the same percentage of red fruits. The day when the first fruit of the wild type control plant (grown under the same conditions as the mutant plants and being at the same developmental stage) enters a certain stage (e.g. breaker stage) can, for example, be taken as the starting point (day 1) from when on periodically (at certain time intervals, e.g. after 1, 2, 3, 4, 5 or 6 days) the number of fruits that are in breaker stage and the number of fruit that are in full red stage are counted (e.g. both for a mutant plant line and the corresponding control plants).

"Delay of breaker stage" refers to the tomato plants, e.g. mutants according to the invention, requiring significantly more days than the appropriate wild type controls for the first fruits and/or for all fruits to have entered breaker stage, e.g. at least 1 more day, preferably at least 2, 3, 4, 5, 6, 7, 8, 9, 10, 11 or 12 more days than the wild type control, when grown under the same conditions.

As used herein, "reduced ethylene production" refers to (statistically significant) reduced amounts of ethylene being produced by tomato fruits, e.g. tomato fruits according to the invention, when compared to the tomato fruits of an appropriate control, e.g. wild type ACO4/ACO4 fruits, during fruit ripening (e.g. at the orange stage and/or at the full red stage). Such ethylene production preferably is measurable by real time ethylene measurements.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a' or" thus usually means "at least one". It is further understood that, when referring to "sequences" herein, generally the actual physical molecules with a certain sequence of sub-units (e.g. amino acids or nucleic acids) are referred to.

Plants and Methods of the Invention

The present invention provides a plant of the species *Solanum lycopersicum* comprising in its genome at least one copy of a mutant allele of the wild type ACO4 gene, wherein said mutant allele results in a reduced expression or no expression of the wild type ACO4 gene and/or wherein the mutant allele encodes a protein having a decreased function or loss-of-function when compared to the wild type protein; and wherein the wild type ACO4 gene encodes a protein comprising at least 95% amino acid sequence identity to SEQ ID NO: 1.

The inventors surprisingly found that *Solanum lycopersicum* plants homozygous for the mutant allele of the wild type ACO4 gene of the present invention produce tomato fruits (aco4/aco4 fruits) having improved ripening characteristics when compared to fruits produced by wild type plants homozygous for the wild type ACO4 gene (ACO4/ACO4 fruits). Particularly, it was found that aco4/aco4 fruits show an increased fruit firmness after the fruits entered the full red stage. It was further surprisingly found that the average fruit size and the average time of fruits to ripen from the breaker stage to the full red stage is not affected by the mutant allele of the ACO4 gene of the present invention. This provides a significant improvement over the prior art. For instance, currently available tomato fruits having a longer shelf life typically also require more days for the fruits to ripen from the breaker stage to the full red stage and/or require an additional treatment, such as a treatment with an external ethylene source, to allow the fruits to fully ripen.

The mutant allele according to the present invention thus preferably causes the fruits having an increased fruit firmness after the fruits entered the full red stage when said mutant allele is present in the plant in homozygous form. In one aspect, the present invention provides a plant of the species *Solanum lycopersicum* comprising the mutant allele as further described herein, wherein said plant is homozygous for the mutant allele. Said plant homozygous for the mutant allele produces fruits (aco4/aco4 fruits) having an increased fruit firmness after the fruits entered the full red stage when compared to control fruits (e.g. ACO4/ACO4 fruits). The present invention thus preferably provides a plant of the species *Solanum lycopersicum* comprising in its genome at least one copy of a mutant allele of the wild type ACO4 gene, wherein said mutant allele results in a reduced expression or no expression of the wild type ACO4 gene and/or wherein the mutant allele encodes a protein having a decreased function or loss-of-function when compared to the wild type protein and wherein the wild type ACO4 gene encodes a protein comprising at least 95% amino acid sequence identity to SEQ ID NO: 1, wherein the plant is homozygous for the mutant allele and said plant produces fruits having an increased fruit firmness after the fruits entered the full red stage, wherein said fruits having an increased fruit firmness have an increased capacity to resist deformation resulting from the application of a defined mechanical force when compared to fruits produced by wild type plants.

Accordingly, the present invention provides a plant of the species *Solanum lycopersicum* producing fruits having at least one copy of a mutant allele of the wild type ACO4 gene. The wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO: 1, (as determined using methods discloses elsewhere herein).

Accordingly, the mutant allele of the of the wild type ACO4 gene leads to a disruption of the normal (wild type) protein function of the protein encoded by ACO4 gene. The mutant allele as described herein thus may result in reduced expression or no expression of the wild type ACO4 gene. The mutant allele as described herein may also encode a protein having a decreased function or loss-of-function when compared to the wild type protein. Thus, the mutant allele that causes an increased fruit firmness when present in homozygous form may be associated with a reduced expression or even a loss of expression of an otherwise functional ACO4 gene product. In a non-limiting example, such a reduced expression or loss of expression may be the result of one or more mutations in a regulatory region of the ACO4 gene, e.g. in a promoter sequence of the ACO4 gene. In a further non-limiting example, such a reduced expression or loss of expression may be the result of one or more mutations in a transcription factor that is required for normal (wild type) expression of the ACO4 gene product (e.g. a functional variant of the wild type ACO4 protein). In a further non-limiting example, such a reduced expression or loss of expression may be the result of posttranscriptional gene silencing or RNAi. Means and methods to determine the expression level of a given gene are well known in the art including, but not limited to, quantitative reverse transcription polymerase chain reaction (quantitative RT-PCR) for the detection and quantification of a specific mRNA and enzyme-linked immunosorbent assay (ELISA) for the detection and quantification of a specific protein. The mutant allele that causes an increased fruit firmness when present in homozygous form may be associated with the expression of a protein having a decreased function or loss-of-function when compared to the wild type protein (e.g. a non-functional variant of the wild type ACO4 protein). In a non-limiting example, such a decreased function or loss-of-function may be the result of a mutation in the coding region of the ACO4 gene, resulting e.g. in one or more amino acids being replaced (e.g. through a frame-shift mutation or due to a missense mutation), inserted or deleted compared to the wild type protein. Means and methods to determine protein function are well known in the art including, but not limited to phenotypic testing assays for normal protein function (e.g. the detection of normal (i.e. non-decreased) decline of fruit firmness), bioassays capable of quantification of enzymatic activity and in silico prediction of amino acid changes that affect protein function, as further described herein above.

In one aspect of the invention therefore concerns plant cells or plants of the species *Solanum lycopersicum* comprising a mutant allele of a ACO4 protein-encoding gene characterized in that the mutant ACO4 allele comprises or effects one or more of the mutations selected from the group consisting of:

(a) a deletion, truncation, insertion, point mutation, nonsense mutation, missense or non-synonymous mutation, splice-site mutation, frame shift mutation in the genomic sequence;

(b) a mutation in one or more regulatory sequences;

(c) a deletion, truncation, insertion, point mutation, nonsense mutation, missense or non-synonymous mutation, splice-site mutation, frame shift mutation in the coding sequence;

(d) a deletion, truncation, insertion, point mutation, nonsense mutation, missense or non-synonymous mutation, splice-site mutation, frame shift mutation in the pre-mRNA or mRNA; and/or (e) a deletion, truncation, insertion or replacement of one or more amino acids in the ACO4 protein.

The above mutant allele results in decreased activity of the mutant ACO4 protein compared to the wild type ACO4 protein in a *Solanum lycopersicum* plant. The decreased activity is due to a knock-out of expression of the ACO4 gene, a knock-down of expression of the gene, a loss of function of the encoded mutant ACO4 protein or a decrease of function of the mutant ACO4 protein. A mutant allele according to the invention may be a "induced mutant allele", i.e. a mutant allele generated by human interventions such as mutagenesis. Suitable mutagenesis methods comprise chemical mutagenesis (e.g. using EMS or MNU mutagenesis or mutagenesis by generating reactive oxygen species) and radiation mutagenesis (e.g. using UV radiation or ion beam radiation). Mutant alleles according to the invention can also be generated by targeted mutagenesis methods, such as gene editing methods including, but not limited to, CRISPR/Cas9-based targeted mutagenesis methods and CRISPR/Cpf1-based targeted mutagenesis methods. Furthermore, a mutant aco4 allele according to the present invention, wherein said mutant allele results in a reduced expression or no expression of the ACO4 gene and/or wherein the mutant allele encodes a protein having a decreased function or loss-of-function when compared to the wild type Solanum lycopersicum ACO4 protein, may also be identified by screening of wild tomato plants (e.g. landraces, PI accession, CGN accessions, etc.) or by screening orthologs of the Solanum lycopersicum ACO4 gene in wild relatives of Solanum lycopersicum. Such a "natural mutant allele" which may be identified in a wild tomato plant and/or a wild relative of Solanum lycopersicum may be introgressed into a cultivated Solanum lycopersicum plant using standard breeding methods to provide a plant according to the present invention. It is preferred that the mutant allele of the present invention is an induced mutant allele. The plant of the present invention preferably is a cultivated Solanum lycopersicum plant.

In one aspect, the present invention provides a plant comprising a mutant allele of the wild type ACO4 gene, wherein the mutant allele as described herein encodes a protein that is truncated when compared to the wild type protein. In one aspect, the truncated ACO4 protein comprises at the most amino acid residues 1-500 of SEQ ID NO:1 or a fragment thereof, which in the context of the present invention means that the truncated protein comprises at the most amino acid residues 1-200 of SEQ ID NO:1 (i.e. amino acid residues starting at, and including, amino acid 1 and ending at the most at, and including, amino acid 200 of SEQ ID NO:1) or any fragment in between said amino acid residues 1-200 of SEQ ID NO:1. For instance, the truncated protein of the present invention comprises at the most amino acid residues 1-150 of SEQ ID NO:1 or a fragment thereof, at the most amino acid residues 1-100 of SEQ ID NO:1 or a fragment thereof or at the most amino acid residues 1-50 of SEQ ID NO:1 or a fragment thereof. In one aspect, the mutant ACO4 allele in the species Solanum lycopersicum is the mutant ACO4 cDNA (mRNA) sequence depicted in SEQ ID NO:4. In one aspect, the mutant ACO4 allele in the species Solanum lycopersicum encodes the mutant ACO4 protein depicted in SEQ ID NO:3.

The plant according to the present invention comprises at least one copy of the mutant allele as provided herewith. Such a plant thus may be heterozygous for the mutant allele of the present invention. Such a heterozygous plant comprises (at least) one copy of the wild type allele and (at least) one copy of the mutant allele of the present invention. Such a heterozygous plant shows a fruit ripening and fruit firmness phenotype similar to wild type plants (i.e. plants homozygous for the wild type ACO4 allele). The present invention thus is also directed to plants comprising the mutant ACO4 allele of the present invention in heterozygous form. Such heterozygous plants can also be advantageously used in accordance with the present invention for breeding to generate offspring that is homozygous for the mutant ACO4 allele as further described herein. In one aspect, the present invention provides a plant that is homozygous for the mutant allele of the present invention. Such a plant is inter alia characterized in that it is capable of producing fruits having an increased fruit firmness after the fruits entered the full red stage, as further described herein. The plant according to the present invention which is homozygous for the mutant allele of the present invention may be further characterized in that said fruits have normal firmness and/or normal ripening until the full red stage. Normal fruit firmness and normal fruit ripening are defined by determining the decrease in fruit firmness and the time required for fruit ripening of fruits produced by control plants which are homozygous for the wild type allele.

The plants of the present invention may be any plant of the species Solanum lycopersicum as described herein, comprising in its genome at least one copy of a mutant allele of the wild type ACO4 gene. In one aspect, the present invention provides a plant as described herein that further is an inbred plant, a dihaploid plant or a hybrid plant. In one aspect, accordingly, the present invention provides that the plant of the present invention is an inbred plant. Such an inbred plant is highly homozygous, for instance by repeated selfing crossing steps. Such an inbred plant may be very useful as a parental plant for the production of F1 hybrid seed. In one aspect, the disclosure provides for haploid plants and/or dihaploid (double haploid) plants of plant of the invention are encompassed herein, which comprise the mutant ACO4 allele as described herein. Haploid and dihaploid plants can for example be produced by anther or microspore culture and regeneration into a whole plant. For dihaploid production chromosome doubling may be induced using known methods, such as colchicine treatment or the like. So, in one aspect a Solanum lycopersicum plant is provided, comprising an increased fruit firmness phenotype as described, wherein the plant is a dihaploid plant. The present invention further provides hybrid plants, which may have advantages such as improved uniformity, vitality and/or disease tolerance.

The plants provided by the present invention may be used to produce fruits. The present invention thus provides the use of a plant of the species Solanum lycopersicum as provided herein as a crop for consumption. Particularly the fruits produced by the plants of the present invention can be advantageously used as a crop for consumption since these fruits have an increased fruit firmness after the fruits entered the full red stage.

The plants provided by the present invention may be used to produce propagation material. Such propagation material comprises propagation material suitable for and/or resulting from sexual reproduction, such as pollen and seeds. Such propagation material comprises propagation material suitable for and/or resulting from asexual or vegetative reproduction including, but not limited to cuttings, grafts, tubers, cell culture and tissue culture. The present invention thus further provides the use of a plant of the species Solanum lycopersicum as provided herein as a source of propagation material.

Seeds

The present invention provides seed from which any plant according to the invention can be grown. Furthermore, the invention provides a plurality of such seed. A seed of the invention can be distinguished from other seeds due to the presence of the mutant allele of the wild type ACO4 gene as described herein, either phenotypically (based on plants capable of producing fruits having the increased fruit firmness phenotype of the present invention) and/or using molecular methods to detect the mutant allele in the cells or tissues, such as molecular genotyping methods to detect the mutant allele of the present invention or sequencing. Accordingly, the present invention provides seed from which any plant according to the invention can be grown, wherein said seed comprises in its genome at least one copy of a mutant allele of the wild type ACO4 gene wherein said mutant allele results in a reduced expression or no expression of the wild type ACO4 gene and/or wherein the mutant allele encodes a protein having a de-creased function or loss-of-function when compared to the wild type protein; and wherein the wild type ACO4 gene encodes a protein comprising at least 95% amino ac-id sequence identity to SEQ ID NO: 1. Seeds include for example seeds produced by a plant of the invention which is heterozygous for the mutant allele after self-pollination and optionally selection of those seeds which comprise one or two copies of the mutant allele (e.g. by non-destructive seed sampling methods and analysis of the presence of the mutant aco4 allele), or seed produced after cross-pollination, e.g. pollination of a plant of the invention with pollen from another solanaceous plant, preferably from another *Solanum lycopersicum* plant, or pollination of another *Solanum lycopersicum* plant with pollen of a plant of the invention.

Particularly, the present invention provides pollen or seed produced by the plant according to the present invention, or seed from which a plant of the invention can be grown, wherein said plant is a plant of the species *Solanum lycopersicum* comprising in its genome at least one copy of a mutant allele of the wild type ACO4 gene, wherein said mutant allele results in a reduced expression or no expression of the wild type ACO4 gene or wherein the mutant allele encodes a protein having a decreased function or loss-of function when compared to the wild type protein, wherein the wild type ACO4 gene encodes a protein comprising at least 95% sequence identity to SEQ ID NO:1, e.g. 96%, 97%, 98%, 98.3%, 98.7%, 99.0%, or 99.3% or more preferably 99.7% sequence identity to SEQ ID NO:1.

Particularly, the present invention provides pollen or seed produced by the plant according to the present invention, or seed from which a plant of the invention can be grown, wherein the pollen or seed comprises the mutant allele of the wild type ACO4 gene as defined as defined herein that is capable of causing an increased fruit firmness fruit phenotype when present in homozygous form. Particularly, the present invention provides seed from which the plant of the present invention can be grown.

The present invention further provides seeds obtained from the methods of producing plants as described herein.

In one aspect, a plurality of seed is packaged into a container (e.g. a bag, a carton, a can etc.). Containers may be any size. The seeds may be pelleted prior to packing (to form pills or pellets) and/or treated with various compounds, including seed coatings.

Plant Parts and Vegetative Reproductions

In a further aspect a plant part, obtained from (obtainable from) a plant of the invention is provided herein, and a container or a package comprising said plant part.

Particularly, the present invention provides a part from the plant of the present invention, wherein the part comprises in its genome at least one copy of the mutant ACO4 allele as described herein, preferably wherein the part is selected from the group consisting of a fruit, leaf, anther, pistil, stem, petiole, root, ovule, pollen, protoplast, tissue, seed, flower, cotyledon, hypocotyl, embryo and cell. The various stages of development of aforementioned plant parts are comprised in the invention.

Particularly, fruit produced by the plant of the present invention is provided. A fruit of the invention can be distinguished from other fruits due to the presence of the mutant allele of the wild type ACO4 gene as described herein, either phenotypically (based on fruits having the increased fruit firmness phenotype of the present invention) and/or using molecular methods to detect the mutant allele in the cells or tissues, such as molecular genotyping methods to detect the mutant allele of the present invention or sequencing. Accordingly, the present invention provides a tomato fruit wherein said tomato fruit comprises in its genome at least one copy of a mutant allele of the wild type ACO4 gene wherein said mutant allele results in a reduced expression or no expression of the wild type ACO4 gene and/or wherein the mutant allele encodes a protein having a decreased function or loss-of-function when compared to the wild type protein; and wherein the wild type ACO4 gene encodes a protein comprising at least 95% amino ac-id sequence identity to SEQ ID NO: 1. Plants according to the present invention may be heterozygous for the mutant allele of the ACO4 gene. The fruits produced by such heterozygous plants may already show a phenotype that can be distinguished from fruits produced by a comparable plant that is homozygous for a wild type allele of the ACO4 gene. Preferably, the fruit is homozygous for the mutant allele of the ACO4 gene and has an increased fruit firmness after the fruits entered the full red stage. The present invention further provides a (processed) food product comprising the fruit produced by the plant as described herein. Preferably, the fruit comprised in said (processed) food product is produced by a plant that is homozygous for the mutant allele of the ACO4 gene and accordingly has an increased fruit firmness after the fruits entered the full red stage.

Preferably, the fruit homozygous for the mutant allele of the ACO4 gene does not show a (statistically significant) difference in fruit size when compared to the fruits of genetically identical plants comprising at least one copy of a wild type allele of the ACO4 gene. Furthermore, the fruit homozygous for the mutant allele of the ACO4 gene preferably does not show a (statistically significant) difference in the number of days required for the fruits to ripen from the breaker stage to the full red stage when compared to the fruits of genetically identical plants comprising at least one copy of a wild type allele of the ACO4 gene. It was surprisingly found in the context of the present invention that the fruits produced by the plants according to the present invention have a normal shape and size. It was further surprisingly found in the context of the present invention that the fruits produced by the plants according to the present invention have a normal fruit firmness and/or normal ripening during the fruit ripening stages that precede the full red stage. The present invention therefore for the first time provides tomato fruit produced by a *Solanum lycopersicum* plant wherein the shelf life is extended when compared to the fruits of genetically identical wild type plants (i.e. plants comprising at least one copy of a wild type allele of the ACO4 gene) without having disadvantageous effects on fruit size or ripening behaviour, such as colour development and/or ripening time of the fruits required to reach the full red stage.

The present invention further provides a part of the plant according to the present invention, wherein said plant part may be a leaf, anther, pistil, stem, petiole, root, ovule, pollen, protoplast, tissue, seed, flower, cotyledon, hypocotyl, embryo or cell.

In a further aspect, the plant part is a plant cell. In still a further aspect, the plant part is a non-regenerable cell or a regenerable cell. In another aspect the plant cell is a somatic cell.

A non-regenerable cell is a cell which cannot be regenerated into a whole plant through in vitro culture. The non-regenerable cell may be in a plant or plant part (e.g. leaves) of the invention. The non-regenerable cell may be a cell in a seed, or in the seedcoat of said seed. Mature plant organs, including a mature leaf, a mature stem or a mature root, contain at least one non-regenerable cell.

In a further aspect the plant cell is a reproductive cell, such as an ovule or a cell which is part of a pollen. In an aspect, the pollen cell is the vegetative (non-reproductive) cell, or the sperm cell (Tiezzi, Electron Microsc. Review, 1991). Such a reproductive cell is haploid. When it is regenerated into whole a plant, it comprises the haploid genome of the starting plant. If chromosome doubling occurs (e.g. through chemical treatment), a double haploid plant can be regenerated. In one aspect the plant of the invention comprising the mutant ACO4 allele is a haploid or a double haploid *Solanum lycopersicum* plant according to the present invention.

Moreover, there is provided an in vitro cell culture or tissue culture of the *Solanum lycopersicum* plant of the invention in which the cell- or tissue culture is derived from a plant part described above, such as, for example and without limitation, a leaf, a pollen, an embryo, cotyledon, hypocotyls, callus, a root, a root tip, an anther, a flower, a seed or a stem, or a part of any of them, or a meristematic cell, a somatic cell, or a reproductive cell.

The present invention further provides a vegetatively propagated plant, wherein said plant is propagated from a plant part according to the present invention.

Further, isolated cells, in vitro cell cultures and tissue cultures, protoplast cultures, plant parts, harvested material (e.g. harvested tomato fruits), pollen, ovaries, flowers, seeds, stamen, flower parts, etc. comprising in each cell at least one copy of the mutant ACO4 allele of the present invention are provided. Thus, when said cells or tissues are regenerated or grown into a whole *Solanum lycopersicum* plant, the plant comprises the mutant allele capable of causing an increased fruit firmness after the fruits entered the full red stage when present in homozygous form.

Thus, also an in vitro cell culture and/or tissue culture of cells or tissues of plants of the invention is provided. The cell or tissue culture can be treated with shooting and/or rooting media to regenerate a *Solanum lycopersicum* plant.

Also vegetative or clonal propagation of plants according to the invention is encompassed herein. Many different vegetative propagation techniques exist. Cuttings (nodes, shoot tips, stems, etc.) can for example be used for in vitro culture as described above. Also other vegetative propagation techniques exist and can be sued, such as grafting, or air layering. In air layering a piece of stem is allowed to develop roots while it is still attached to the parent plant and once enough roots have developed the clonal plant is separated from the parent.

Thus, in one aspect a method is provided comprising:
(a) obtaining a part of a plant of the invention (e.g. cells or tissues, e.g. cuttings),
(b) vegetatively propagating said plant part to generate an identical plant from the plant part.

Thus, also the use of vegetative plant parts of plants of the invention for clonal/vegetative propagation is an aspect of the invention. In one aspect a method is provided for vegetatively reproducing a *Solanum lycopersicum* plant of the invention comprising two copies of a mutant ACO4 allele is provided. Also a vegetatively produced plant comprising two copies if a mutant ACO4 allele is provided.

In another aspect a plant of the invention, comprising two copies of the mutant ACO4 allele according to the invention, is propagated by somatic embryogenesis techniques.

Also provided is a *Solanum lycopersicum* plant regenerated from any of the above-described plant parts, or regenerated from the above-described cell or tissue cultures, said regenerated plant comprising in its genome at least one copy of a mutant allele of the wild type ACO4 gene, wherein said mutant allele results in a reduced expression or no expression of the wild type ACO4 gene or wherein the mutant allele encodes a protein having a decreased function or loss-of function when compared to the wild type protein, wherein the wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1. This plant can also be referred to as a vegetative propagation of plants of the invention. Preferably, the regenerated plant is homozygous for the mutant ACO4 allele of the present invention and thus is capable of producing fruits having an increased fruit firmness after the fruits entered the full red stage.

The invention also relates to a food or feed product comprising or consisting of a plant part described herein. The food or feed product may be fresh or processed, e.g., canned, steamed, boiled, fried, blanched and/or frozen etc. Examples are sandwiches, salads, juices, sauces, fruit pastes, ketchup or other food products comprising a fruit or a part of a fruit of a plant of the invention.

The present invention further provides the use of a nucleic acid encoding the ACO4 protein for the identification of a plant of the species *Solanum lycopersicum* capable of producing fruits having an increased fruit firmness after the fruits entered the full red stage, wherein said ACO4 protein comprises at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1.

The present invention further provides the use of a nucleic acid encoding the ACO4 protein for breeding plants of the species *Solanum lycopersicum* capable of producing fruits having an increased fruit firmness after the fruits entered the full red stage, wherein said ACO4 protein comprises at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1.

Plants and Progeny

In another aspect, plants and parts of *Solanum lycopersicum* plants of the invention, and progeny of *Solanum lycopersicum* plant of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises at least one copy of the mutant ACO4 allele of the present invention.

The present invention further provides a plant of the species *Solanum lycopersicum* grown from the seed as described herein. The present invention thus provides a *Solanum lycopersicum* plant grown from seeds obtained from the method for producing a *Solanum lycopersicum* plant as described herein.

Furthermore, the invention provides progeny comprising or retaining the increased fruit firmness phenotype as described herein (conferred by the mutant ACO4 allele), such as progeny obtained by, e.g., selfing one or more times and/or cross-pollinating a plant of the invention with another *Solanum lycopersicum* plant of a different variety or breeding line of the same plant species (or of a plant species that can be crossed with the *Solanum lycopersicum* plant of the present invention), or with a *Solanum lycopersicum* plant of the invention one or more times. In particular, the invention provides progeny homozygous for the mutant ACO4 allele capable of producing fruit having an increased fruit firmness after the fruits entered the full red stage. In one aspect the invention relates to for a progeny plant comprising the mutant ACO4 allele, such as a progeny plant that is produced from a *Solanum lycopersicum* plant comprising the mutant ACO4 allele by one or more methods selected from the group consisting of: selfing, crossing, mutation, double haploid production or transformation. Mutations preferable are human induced mutations or somaclonal mutations. In one aspect, plants or seeds of the invention may also be mutated (by e.g. irradiation, chemical mutagenesis, heat treatment, TILLING, targeted mutagenesis, etc.) and/or mutated seeds or plants may be selected (e.g. somaclonal variants, etc.) in order to change one or more characteristics of the plants. Similarly, plants of the invention may be transformed and regenerated, whereby one or more chimeric genes are introduced into the plants. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the mutant ACO4 allele and, when the mutant ACO4 allele is comprised in homozygous form, the an increased fruit firmness phenotype conferred by it and contains the desired trait.

In another aspect the invention relates to a method for producing seed, comprising crossing a plant of the invention with itself or a different plant and harvesting the resulting seed. In a further aspect the invention relates to seed produced according to this method and/or a plant produced by growing such seed. Thus, a plant of the invention may be used as male and/or female parent, in the production of seeds, whereby the plants grown from said seeds comprise the mutant ACO4 allele as provided herewith. The present invention thus further provides a plant grown from the seed provided by the present invention.

Thus, in one aspect progeny of a *Solanum lycopersicum* plant of the invention are provided, wherein the progeny plant is produced by selfing, crossing, mutation, double haploid production or transformation and preferably wherein the progeny retain the mutant ACO4 allele.

The present invention further provides a method of producing tomato fruit having an increased shelf life, said method comprising growing a plant according to the present invention and harvesting the fruits produced by said plants. Preferably, the plant producing the tomato fruit having an increased shelf life according to the method of the present invention is homozygous for the mutant ACO4 allele as described herein and accordingly has an increased fruit firmness after the fruits entered the full red stage (when compared to the fruits of genetically identical wild type plants, i.e. plants comprising at least one copy of a wild type allele of the ACO4 gene).

The present invention further provides a method of identifying and/or selecting a plant or plant part of the species *Solanum lycopersicum* comprising a mutant allele of the wild type ACO4 gene comprising determining whether the plant or plant part comprises a mutant allele of the ACO4 gene, wherein said mutant allele results in reduced expression or no expression of the wild type ACO4 gene or wherein the mutant allele encodes a protein having a decreased function or loss-of function when compared to the wild type protein and optionally selecting a plant or plant part comprising at least one copy of a mutant allele of the ACO4 gene, wherein the wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1. As described herein, the mutant allele of the present invention when present in homozygous form causes the fruits having an increased fruit firmness after the fruits entered the full red stage. Accordingly, the present invention provides a method of identifying and/or selecting a plant or plant part of the species *Solanum lycopersicum* comprising determining whether the plant or plant part comprises a mutant allele of the ACO4 gene, wherein said mutant allele results in reduced expression or no expression of the wild type ACO4 gene or wherein the mutant allele encodes a protein having a decreased function or loss-of function when compared to the wild type protein and optionally selecting a plant or plant part comprising at least one copy of a mutant allele of the ACO4 gene, wherein the wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1 and wherein the mutant allele when present in homozygous form causes the fruits having an increased fruit firmness after the fruits entered the full red stage.

The method comprises screening at the DNA, RNA (or cDNA) or protein level using known methods, in order to detect the presence of the mutant allele according to the present invention. There are many methods to detect the presence of a mutant allele of a gene.

For example, if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example, the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method.

Equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Molecular markers may also be used to aid in the identification of the plants (or plant parts or nucleic acids obtained therefrom) containing the mutant ACO4 allele. For example, one can develop one or more suitable molecular markers which are closely genetically (and preferably also physically) linked to the mutant ACO4 allele. Most preferably, the causal gene mutation is used as the molecular marker used for the identification of the plants (or plant parts or nucleic acids obtained therefrom) containing the mutant ACO4 allele. Suitable molecular markers can be developed by crossing a *Solanum lycopersicum* plant according to the present invention (preferably capable of producing fruits having an increased fruit firmness after the fruits entered the full red stage) with a wild type plant and developing a segregating population (e.g. F2 or backcross population) from that cross. The segregating population can then be phenotyped for the increased fruit firmness phenotype as described herein and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the increased fruit firmness trait of the present invention in the segregating population can be identified and their order and genetic distance (centimorgan distance, cM) to the ACO4 gene (or locus) can be identified. Molecular markers which are closely linked to ACO4 locus, e.g. markers at a 5 cM distance or less, can then be used in detecting and/or selecting plants (e.g. plants of the invention or progeny of a plant of the invention) or plant parts comprising or retaining the mutant ACO4 allele (e.g. in an introgression fragment). Such closely linked molecular markers can replace phenotypic selection (or be used in addition to phenotypic selection) in breeding programs, i.e. in Marker Assisted Selection (MAS). Preferably, linked markers are used in MAS. More preferably, flanking markers are used in MAS, i.e. one marker on either side of the locus of the mutant ACO4 allele.

Preferably, the plant or plant part is subjected to a mutation inducing step prior to determining whether the plant or plant part comprises a mutant allele of an ACO4 gene. Said mutation inducing step may comprise contacting said plant or plant part with a mutagen. Accordingly, the present invention provides a method comprising contacting a plant or plant part of the species *Solanum lycopersicum* with a mutagen followed by identifying and/or selecting a plant or plant part comprising a mutant allele of the wild type ACO4 gene as described herein. Accordingly, said step of identifying and/or selecting a plant or plant part of the species *Solanum lycopersicum* comprising a mutant allele of the wild type ACO4 gene comprises determining whether the plant or plant part comprises a mutant allele of the ACO4 gene, wherein said mutant allele results in a reduced expression or no expression of the wild type ACO4 gene or wherein the mutant allele encodes a protein having a decreased function or loss-of function when compared to the wild type protein and optionally selecting a plant or plant part comprising at least one copy of a mutant allele of the ACO4 gene, wherein the wild type ACO4 gene encodes a protein comprising at least 95% amino acid sequence identity to SEQ ID NO:1. Mutagenesis methods particularly useful in the context of the present invention include chemical mutagenesis (e.g. EMS or MNU mutagenesis or mutagenesis by generating reactive oxygen species) or other untargeted mutagenesis methods (e.g. by radiation mutagenesis using e.g. UV radiation or ion beam radiation). Said mutation inducing step may also encompass targeted mutagenesis methods such as genome editing using engineered nucleases. In such genome editing methods a site-specific double-strand break is induced in a target cell using an engineered nuclease upon which said double strand break may be repaired by the cell's endogenous DNA double stranded break repair mechanisms (e.g. the homology directed repair mechanism), which allows a site-specific deletion, modification, insertion or replacement of DNA in a target cell. Engineered nucleases useful in genome editing methods include meganucleases, zinc finger nucleases (ZFNs), transcription activator-like effector-based nucleases (TALEN), and clustered regularly interspaced short palindromic repeats (CRISPR)-associated nucleases. Genome editing methods particularly useful in the context of the present invention include, but are not limited to, CRISPR/Cas9-based targeted mutagenesis methods and CRISPR/Cpf1-based targeted mutagenesis methods; see e.g. Brooks et al. (2014) Plant Physiol 166, 1292-1297 and WO2016/205711 A1.

Preferably, the plant material that is subjected to a mutation inducing step comprises a wild type ACO4 allele in homozygous form. The mutation inducing step subsequently causes a mutation in the wild type ACO4 allele to provide a mutant ACO4 allele that is capable of the increased fruit firmness phenotype of the present invention.

Also transgenic plants can be made to introduce the mutant ACO4 allele of the invention using known plant transformation and regeneration techniques in the art. An "elite event" can be selected, which is a transformation event having the chimeric gene (comprising a promoter operably linked to a nucleotide sequence encoding a loss-of-function ACO4 protein or reduced-function ACO4 protein) inserted in a particular location in the genome, which results in good expression of the desired phenotype. Also transgenic plants can be made comprising a construct which reduces or abolishes the expression of the endogenous (wild type) ACO4 gene, such as an RNAi construct.

The present invention accordingly provides a method of producing a *Solanum lycopersicum* plant of the invention comprising the steps of:
(a) obtaining plant material from a plant of the species *Solanum lycopersicum*;
(b) subjecting said plant material to mutagenesis to create mutagenized plant material;
(c) analyzing said mutagenized plant material to identify a plant having at least one mutation in ACO4 gene, wherein the wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1.

TILLING (Targeting Induced Local Lesions IN Genomes) is a general reverse genetics method that uses traditional untargeted mutagenesis methods to create libraries of mutagenized individuals that are later subjected to high throughput screens for the discovery of specific mutations. TILLING typically combines chemical mutagenesis with mutation screens of pooled PCR products, resulting in the isolation of missense and non-sense mutant alleles of the targeted genes. Thus, TILLING uses untargeted mutagenesis methods as described herein, followed by high-throughput screening for mutations in specific target genes, such as the ACO4 gene according to the invention. S1 nucleases, such as CEL1 or ENDO1, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, including solanaceous plants such as tomato. (see http://tilling.ucda-vis.edu/index.php/Tomato_Tilling), rice (Till et al. 2007, BMC Plant Biol 7: 19), *Arabidopsis* (Till et al. 2006, Methods Mol Biol 323: 127-35), *Brassica*, maize (Till et al. 2004, BMC Plant Biol 4: 12), etc. Also EcoTILLING, whereby mutants in natural populations are detected, also has been described, see Till et al. 2006 (Nat Protoc 1: 2465-77) and Comai et al. 2004 (Plant J 37: 778-86).

In one aspect of the invention (cDNA or genomic) nucleic acid sequences encoding mutant ACO4 proteins comprise one or more non-sense and/or missense mutations, e.g. transitions (replacement of purine with another purine (A↔G) or pyrimidine with another pyrimidine (C↔T)) or transversions (replacement of purine with pyrimidine, or vice versa (C/T↔A/G). In one aspect the non-sense and/or missense mutation(s) is/are in the nucleotide sequence encoding any of the ACO4 exons, or an essentially similar domain of a variant ACO4 protein, i.e. in a domain comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1.

In one aspect a ACO4 nucleotide sequence comprising one or more non-sense and/or mis-sense mutations in one of the exon-encoding sequence are provided, as well as a plant comprising such a mutant allele resulting in a plant capable of producing fruits having an increased fruit firmness after the fruits entered the full red stage when said mutant allele is present in homozygous form.

In one aspect, accordingly, the plant or plant part is identified and/or selected from a TILLING population that was obtained by subjecting plants or plant parts to a mutagen. Thus, in one aspect a method for producing a is provided comprising the steps of:
(a) providing a TILLING population of a plant of the species *Solanum lycopersicum*, wherein said TILLING population is preferably obtained by subjecting a plant or a plant part to a mutagen,
(b) screening said TILLING population for mutants in the ACO4 gene, wherein the wild type ACO4 gene encodes a protein comprising at least 95% amino acid sequence identity to SEQ ID NO:1, e.g. 96%, 97%, 98%, 98.3%, 98.7%, 99.0%, or 99.3% or more preferably 99.7% sequence identity to SEQ ID NO:1, and
(c) selecting from the mutant plants of (b) those plants (or progeny of those plants) which are capable of producing fruits having an increased fruit firmness after the fruits entered the full red stage.

Mutant plants (M1) are preferably selfed one or more times to generate for example M2 populations or preferably M3 or M4 populations for phenotyping. In M2 populations the mutant allele is present in a ratio of 1 (homozygous for mutant allele): 2 (heterozygous for mutant allele): 1 (homozygous for wild type allele).

The present invention further provides a method of producing a plant of the species *Solanum lycopersicum* comprising in its genome at least one copy of a mutant allele of the ACO4 gene, wherein said mutant allele results in a reduced expression or no expression of the wild type ACO4 gene or wherein the mutant allele encodes a protein having a decreased function or loss-of function when compared to the wild type protein, said method comprising the step(s) of:
(i) crossing a first *Solanum lycopersicum* plant and a second plant, wherein the first *Solanum lycopersicum* plant is the plant according to the present invention;
(ii) optionally harvesting seed from the crossing of (i) and selecting seed comprising in its genome at least one copy of a mutant allele of the ACO4 gene as described herein.

Preferably, both the first *Solanum lycopersicum* plant and the second *Solanum lycopersicum* plant in step (i) of the method of producing the *Solanum lycopersicum* plant as provided herein are plants according to the present invention. More preferably, both the first *Solanum lycopersicum* plant and the second *Solanum lycopersicum* plant in step (i) of the method of producing the *Solanum lycopersicum* plant as provided herein are plants according to the present invention homozygous for the mutant allele.

The present invention further provides a plant grown from seeds obtained by the method of identifying and/or selecting a plant or plant part of the species *Solanum lycopersicum* comprising a mutant allele of the ACO4 gene as described herein. The present invention further provides a plant grown from seeds obtained by the method of producing a plant of the species *Solanum lycopersicum* comprising in its genome at least one copy of a mutant allele of the ACO4 gene as defined herein.

The present invention further provides a method of producing a plant of the species *Solarium lycopersicum* capable of producing fruits having an increased fruit firmness after the fruits entered the full red stage by growing a seed according to the present invention.

In one aspect, the increased fruit firmness trait of the present invention is caused by a mutation in the ACO4 allele or orthologous allele or homologous allele. In one aspect, accordingly, a specific mutant ACO4 allele is provided.

In one aspect plants, especially in respect of the European Patent Convention, the plant according to the invention is not exclusively obtained by means of an essentially biological process, as for instance defined by Rule 28(2) EPC. If such a disclaimer is present in the claim of the European patent, it should be noted that using a plant comprising a mutant allele according to the present invention (e.g. a commercial variety of the applicant) to cross the mutant allele into a different background of *Solarium lycopersicum* will still be seen as falling under the claim, even though an exclusively essentially biological process (only crossing and selection) may have been used to transfer the allele into a different background.

Other embodiments of the invention relate to the following embodiments, which are not to be seen in isolation but can be combined with any of the other embodiments described herein. Preferably, the herein-below described cell or cells is a non-regenerable cell as defined herein above. Alternatively, the herein-below described cell or cells is a non-propagating cell. As used herein, the term "non-propagating plant cell" is a plant cell which is unable to maintain its life by synthesizing carbohydrate and protein from the inorganic substance, such as water, carbon dioxide and mineral salt and so on through photosynthesis.

In one embodiment the present invention provides a cell of a plant of the species *Solanum lycopersicum* comprising in its genome at least one copy of a mutant allele of the wild type ACO4 gene, wherein said mutant allele results in a reduced expression or no expression of the wild type ACO4 gene and/or wherein the mutant allele encodes a protein having a decreased function or loss-of-function when compared to the wild type protein; and wherein the wild type ACO4 gene encodes a protein comprising at least 95% amino acid sequence identity to SEQ ID NO: 1.

The cell according to the preceding embodiment, wherein the mutant allele when present in homozygous form causes the plant to produce fruits having an increased fruit firmness after the fruits entered the full red stage.

The cell according to the preceding embodiments, wherein the plant is homozygous for the mutant allele.

The cell according to the preceding embodiments, wherein the mutant allele encodes a protein that is truncated when compared to the wild type protein.

The cell according to the preceding embodiments, wherein said fruits having an in-creased fruit firmness after the fruits entered the full red stage have normal fruit firmness and/or normal ripening until the full red stage.

The cell according to the preceding embodiments, wherein the plant is an inbred plant, a dihaploid plant or a hybrid plant.

Use of a plant of the species *Solanum lycopersicum* as described herein as a crop for producing fruits for consumption.

Use of a plant of the species *Solanum lycopersicum* as described herein as a source of propagation material.

EXAMPLES

Example 1

Random mutagenesis followed by forward screening method useful for identifying tomato mutant with improved ripening characteristics.

Mutations can be induced by Ionizing radiation produces both DNA strand breaks and oxidative DNA lesions by generating ROS. One of the oxidation products induced by ROS is 8-oxo-7-hydrodeoxyguanosine (8-oxo-dG) that can induce a G/C-to-T/A transversion in the DNA. Mutations can be generated in pollen by harvesting flower buds and irradiate them at room temperature with various doses of, e.g. 100 Gy, γ-rays from a $^{60}$Co source (Akbudak & Seniz (2009) New Zealand Journal of Crop and Horticultural Science 37:361-367). The irradiated pollen containing mutations varying from single base substitutions or deletions to large deletions spanning several mega bases can be used to cross untreated plants (Ryouhei Morita, et al. (2009) Genes Genet Syst.84:361-70). Seeds from the cross (F1) can be sowed again and viable seeds will grow out to generate plants with each its own set of specific mutations. Seeds from the F1 can be collected per plant and grown in turn to be phenotyped. The mutations segregate in the F2 families and their phenotypic effects can be evaluated. The segregation ratio is suggestive for the recessive or dominant nature of the mutation.

Example 2

Random mutagenesis followed by reverse screening from TILLING mutant population.

A highly homozygous inbred line used in commercial tomato breeding can be used for mutagenesis treatment with the following protocol. After seed imbibition on damp Whatman® paper for 24 h, ~20,000 seeds, divided in 8 batches of 2500 respectively, is soaked in 100 ml of ultra-pure water and ethyl methanesulfonate (EMS) at a concentration of 1% in conical flasks. The flasks are gently shaken for 16 h at room temperature. Finally, EMS is rinsed out under flowing water. Following EMS treatment, seeds are directly sown in the greenhouse. Out of the seeds that germinate, a sufficient number of plantlets are transplanted in the field. From these plantlets, at least one fruit is harvested from the surviving and plant bearing plants. For instance, from each remaining M1 mutant plant one fruits is harvested and its seeds isolated. From the obtained population, named M2 population, specific families may be excluded from the population due to low seed set.

DNA is extracted from a pool of 10 seeds originating from each M2 seed lot. Per mutant line, 10 seeds are pooled in a Micronic® deepwell tube; world wide web at micronic.com from a 96 deep-well plate, 2 stainless balls are added to each tube. The tubes and seeds are frozen in liquid nitrogen for 1 minute and seeds are immediately ground to a fine powder in a Deepwell shaker (Vaskon 96 grinder, Belgium; world wide web at vaskon.com) for 2 minutes at 16.8 Hz (80% of the maximum speed). 300 µl Agowa® Lysis buffer P from the AGOWA® Plant DNA Isolation Kit world wide web at agowa.de is added to the sample plate and the powder is suspended in solution by shaking 1 minute at 16.8 Hz in the Deepwell shaker. Plates are centrifuged for 10 minutes at 4000 rpm. 75 µl of the supernatant is pipetted out to a 96 Kingfisher plate using a Janus MDT® (Perkin Elmer, USA; world wide web at perkinelmer.com) platform (96 head). The following steps are performed using a Perkin Elmer Janus® liquid handler robot and a 96 Kingfisher® (Thermo labsystems, Finland; world wide web at thermo.com). The supernatant containing the DNA is diluted with binding buffer (150 µl) and magnetic beads (20 µl). Once DNA is bound to the beads, two successive washing steps are carried out (Wash buffer 1: Agowa wash buffer 1⅓, ethanol ⅓, isopropanol ⅓; Wash buffer 2: 70% ethanol, 30% Agowa wash buffer 2) and finally eluted in elution buffer (100 µl MQ, 0,025 µl Tween).

Grinding ten *S. lycopersicum* seeds generally produces enough DNA to saturate the magnetic beads, thus highly homogenous and comparable DNA concentrations of all samples are obtained. Comparing with lambda DNA references, a concentration of 30 ng/µl for each sample is estimated. Two times diluted DNA was 4-fold flat pooled. 2 µl pooled DNA was used in multiplex PCRs for mutation detection analysis.

High Resolution Melt curve analysis (HRM) is proven to be sensitive and high-throughput methods in human and plant genetics. HRM is a non-enzymatic screening technique. During the PCR amplification dye (LCGreen+dye, Idaho Technology Inc., UT, USA) molecules intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that is recorded as a melting curve by the fluorescence detector. Pools containing a mutation form hetero duplexes in the post-PCR fragment mix. These are identified as differential melting temperature curves in comparison to homo duplexes.

Primers useful to amplify gene fragments for HRM are designed using a computer program (Primer3, http://primer3.sourceforge.net/). The length of the amplification product is limited between 200 and 400 base pairs. Quality of the primers is determined by a test PCR reaction that should yield a single product.

Polymerase Chain Reaction (PCR) to amplify gene fragments can be performed as follows. 10 ng of genomic DNA is mixed with 4 µl reaction buffer (5× Reaction Buffer), 2 µl 10×LC dye ((LCGreen+dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 10 µl. Reaction conditions were: 30 s 98° C., then 40 cycles of 10 s. 98° C., 15 s 60° C., 25 s of 72° C. and finally 60 s at 72° C.

The presence of a particular mutation in individual plants is confirmed by repeating the HRM analysis on DNA from the individual M2 seed lots of the identified corresponding DNA pool. When the presence of the mutation, based on the HRM profile, is confirmed in one of the four individual M2 family DNA samples, the PCR fragments are sequenced to identify the mutation in the gene.

Once the mutation is known the effect of such a mutation can be predicted, using a computer program to identify conserved protein domains, e.g. the Conserved Do-main Database (world wide web at ncbi.nlm.nih.gov/cdd/) is a resource for the annotation of functional units in proteins. Domains can be thought of as distinct functional and/or structural units of a protein. Domains are often identified as recurring (conserved) sequence or structural units, which may exist in various contexts. Modifications in conserved amino acids in conserved domains lead more often to an effect in protein activity than amino ac-ids that vary in homologous proteins from different origin (species, genera or families).

Seeds from M2 families that contain mutations with predicted effect on protein activity are sown for phenotypic analysis of the plants. Homozygous mutants are selected or obtained after selfing and subsequent selection. The effect of the mutation on the corresponding protein and phenotype of the plant is subsequently determined, for instance by using the methods as described herein below.

Example 3

Characterization of tomato fruit firmness according to the present invention.

Seeds from wild type cv. Tapa and mutant W203* in the same genetic background were sown and the seedlings were grown under standard growing conditions in the greenhouse. Six plants were grown for each genotype; mutant W203* with the mutation homozygously or heterozygously present and plants without the mutation ("azygous"), all derived from the same M2 mutant family and wild type plants.

Three comparable clusters of tomatoes were selected on each plant. Each cluster was labelled with a colour label that indicated the cluster age; the oldest cluster (#1) was marked with a yellow label, the second oldest cluster (#2) was marked with a blue label and the third oldest cluster (#3) was marked with a red label. The 3rd and 4th tomato of each cluster were selected for measurement of firmness. By this, six tomatoes where followed from each plant. For every tomato the date of the breaker stage (breakdown of chlorophyll), the orange stage and full red were recorded, classified according to USDA (1997). The colour of the tomato represents the stage of development and therefore a colour chart (Royal Horticultural Society, 2007) was used to determine (the range of) colour(s) that belongs to a ripening stage (Table 1). Tomatoes that entered the breaker stage were marked with a white label at the joint. Every 2 days the population was checked for fruit entering the breaker stage. The fruits were collected for measurement at the day they were just full red.

TABLE 1

Tomato ripening stage is determined by the tomato colour
(RHS Colour chart, Royal Horticultural Society, 2007)

| Tomato ripening stage | Colour code(s) |
| --- | --- |
| Mature green | 144B |
| Breaker | N144D |
| Orange | N163C/D |
| Full Red | 44A/B |

Harvested tomatoes were stored at room temperature (22-24° C.) until measurement after either 0, 7, 14 or 21 days. Firmness was measured using a Single Column Tabletop Testing Systems (Instron, System ID: 3342L2018; Force Transducer model 2519-104) and Bluehill Software (Instron, 825 University Ave, Norwood, MA 02062-2643, USA). Each measurement was carried out only once per fruit and in such a way that the fruits were not damaged. A tomato fruit was compressed between two flat steel plates with an incremental force from 0.1 Newton (N) to 4 (N). Firmness measured as the force (N) necessary to compress fruits per millimetre by the Instron Force Transducer.

The fruit firmness was measured at the day the fruit became full red (0 days after full red) or 7, 14 or 21 days after becoming full red. The results are provided in FIG. 1. Accordingly, it was found that aco4-mutant plants (aco4/aco4 plants) produce fruits having an increased fruit firmness at 21 days after becoming full red when compared to fruits produced by azygous plants (ACO4/ACO4 plants) (P<0.05 Student's T-test).

Figure 2:
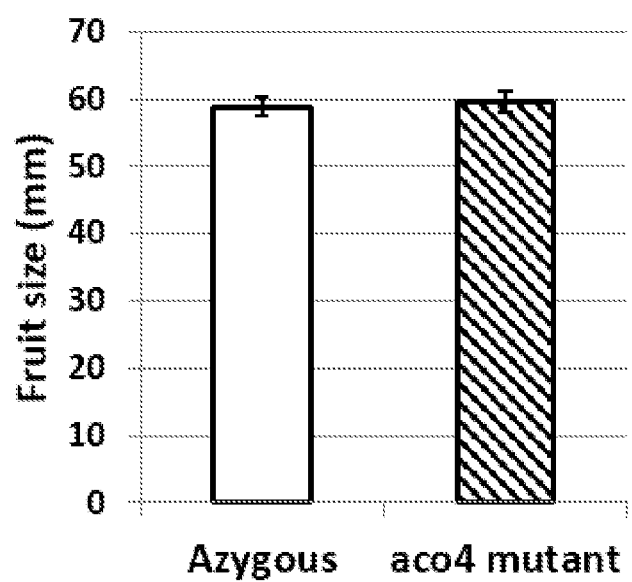
FIG. 2: Comparison of fruit size between mutant plants and azygous plants. Fruit size is measured when fruits reached the full red stage. Cross-diameter in mm of fruits from azygous plants (n=64) and mutant aco4 plants (n=96). Fruit size of azygous and aco4-mutant is not significant different (P=0.84 Student's T-test). The error bars are SE.

It was further found that the size of fruits produced by aco4-mutant plants is not significantly different when compared to fruits produced by azygous plants; see FIG. 2 (P=0.84 Student's T-test).

Figure 3:
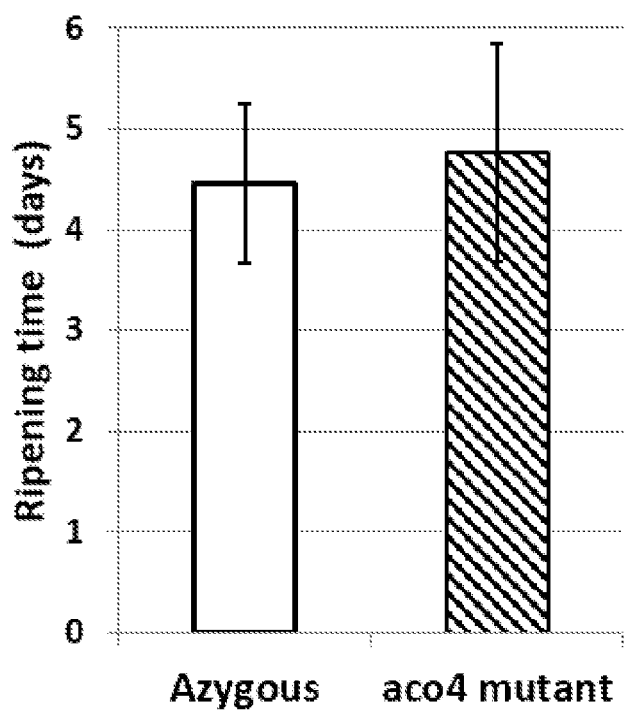
FIG. 3: Comparison of ripening time (days between breaker stage (BR) and fully red stage) between mutant plants and azygous plants. Both genotypes do not differ in time between breaker and full red stage (P=0.35 Student's T-test). The error bars are SE.

It was finally found that the time between breaker stage and full red stage of fruits produced by aco4-mutant plants is not significantly different when compared to fruits produced by azygous plants; see FIG. 3 (P=0.35 Student's T-test).

The invention claimed is:

1. A plant of the species *Solanum lycopersicum* comprising in its genome at least one copy of a mutant allele of the wild type 1-aminocyclopropane-1-carboxylate oxidase 4 (ACO4) gene, wherein said mutant allele encodes a protein having a stop mutation in the Fe(II)-dependent oxygenase domain that results in a truncated protein having a loss of catalytic function of the conversion of 1-aminocyclopropane-1-carboxylic acid to ethylene, and wherein the wild type ACO4 gene encodes a protein comprising at least 95% amino acid sequence identity to SEQ ID NO: 1.

2. The plant according to claim 1, wherein the mutant allele when present in homozygous form causes the fruits to have an increased fruit firmness after the fruits entered the full red stage compared to an isogenic *Solanum lycopersicum* plant without the mutant allele.

3. The plant according to claim 1, wherein the plant is homozygous for the mutant allele.

4. The plant according to claim 2, wherein said fruits having an increased fruit firmness after the fruits entered the full red stage have normal fruit firmness and/or normal ripening until the full red stage.

5. The plant according to claim 1, wherein the plant is an inbred plant, a dihaploid plant or a hybrid plant.

6. A seed from which the plant according to claim 1 can be grown.

7. A fruit produced by the plant according to claim 1.

8. A part of the plant according to claim 1, wherein said plant part is a leaf, anther, pistil, stem, petiole, root, protoplast, tissue, flower, cotyledon or hypocotyl.

9. A method for producing tomato fruit having an increased shelf life, said method comprising growing the plant according to claim 2, producing tomato fruit having an increased shelf life compared to isogenic *Solanum lycopersicum* plant without the mutant allele, and harvesting the fruits produced by said plant.

10. A method of identifying and/or selecting a plant or plant part of the species *Solanum lycopersicum* comprising a mutant allele of the wild type ACO4 gene comprising determining whether the plant or plant part comprises a mutant allele of the ACO4 gene, wherein said mutant allele encodes a protein having a stop mutation in the Fe(II)-dependent oxygenase domain that results in a truncated protein having a loss of catalytic function of the conversion of 1-aminocyclopropane-1-carboxylic acid to ethylene, and optionally selecting a plant or plant part comprising at least one copy of a mutant allele of the ACO4 gene, wherein the wild type ACO4 gene encodes a protein comprising at least 95% amino acid sequence identity to SEQ ID NO: 1.

11. The method according to claim 10, wherein said mutant allele when present in homozygous form causes the fruits to have an increased fruit firmness after the fruits entered the full red stage compared to an isogenic *Solanum lycopersicum* plant without the mutant allele.

12. The method according to claim 10, wherein the plant or plant part is subjected to a mutation inducing step prior to determining whether the plant or plant part comprises a mutant allele of the ACO4 gene.

13. A method of producing a plant of the species *Solanum lycopersicum* comprising in its genome at least one copy of a mutant allele of the ACO4 gene, wherein said mutant allele encodes a protein having a stop mutation in the Fe(II)-dependent oxygenase domain that results in a truncated protein having a loss of catalytic function of the conversion of 1-aminocyclopropane-1-carboxylic acid to ethylene, said method comprising the step(s) of:
  (i) crossing a first *Solanum lycopersicum* plant and a second plant, wherein the first *Solanum lycopersicum* plant is the plant according to claim 1;
  (ii) harvesting seed from the crossing of (i);
  (iii) selecting seed comprising in its genome at least one copy of the mutant allele of the ACO4 gene; and
  (iv) growing said seed to produce a plant comprising in its genome at least one copy of the mutant allele of the ACO4 gene.

14. The method of claim 13, wherein in step (i) both the first *Solanum lycopersicum* plant and the second plant are plants according to claim 1.

15. A seed obtained from the method of claim 13, wherein said seed comprises in its genome at least one copy of the mutant allele of the ACO4 gene.

16. A plant grown from the seed of claim 6.

17. A method of producing a plant of the species *Solanum lycopersicum* by growing the seed of claim 7.

* * * * *